(12) United States Patent
Elman

(10) Patent No.: US 11,103,609 B2
(45) Date of Patent: Aug. 31, 2021

(54) DEVICES AND METHODS FOR CONTROLLED RELEASE OF SUBSTANCES

(71) Applicant: Noel Elman, Brookline, MA (US)

(72) Inventor: Noel Elman, Brookline, MA (US)

(73) Assignee: Noel Elman, Brookline, MA (US)

( * ) Notice: Subject to any disclaimer, the term of this patent is extended or adjusted under 35 U.S.C. 154(b) by 0 days.

(21) Appl. No.: 16/978,192

(22) PCT Filed: Mar. 15, 2019

(86) PCT No.: PCT/IB2019/052121
§ 371 (c)(1),
(2) Date: Sep. 4, 2020

(87) PCT Pub. No.: WO2019/175844
PCT Pub. Date: Sep. 19, 2019

(65) Prior Publication Data
US 2021/0038754 A1    Feb. 11, 2021

Related U.S. Application Data

(60) Provisional application No. 62/643,769, filed on Mar. 16, 2018.

(51) Int. Cl.
*A61L 9/03* (2006.01)
*A01N 25/34* (2006.01)
*A61L 9/12* (2006.01)

(52) U.S. Cl.
CPC ............... *A61L 9/03* (2013.01); *A01N 25/34* (2013.01); *A61L 9/12* (2013.01); *A61L 2209/131* (2013.01)

(58) Field of Classification Search
CPC ........ A61L 9/03; A61L 9/12; A61L 2209/131; A01N 25/34
See application file for complete search history.

(56) References Cited

U.S. PATENT DOCUMENTS 4,809,912 A * 3/1989 Santini .................... A61L 9/042
239/60
6,682,582 B1   1/2004 Carr et al.
(Continued)

OTHER PUBLICATIONS

Wikipedia, Hydrophobic effect (Year: 2016).*
(Continued)

*Primary Examiner* — Sean E Conley
*Assistant Examiner* — Brendan A Hensel
(74) *Attorney, Agent, or Firm* — Nathan & Associates; Menachem Nathan

(57) ABSTRACT

A controlled release device and method of use, the device comprising a reservoir wherein the reservoir is divided into one or more chambers; a first active material placed in a first chamber of the one or more chambers and at least one second active material placed in at least one other of the one or more chambers wherein the first active material comprises an active ingredient (AI), wherein the AI is one of an insecticide, a spatial repellent, a herbicide or a larvicide; wherein the at least one second active material comprises one or both of a matrix and an altering material; a permeable membrane covering the first chamber; partitions positioned between adjacent chambers of the one or more chambers for dividing the reservoir into chambers such that full or partial removal of one or more of the partitions results in mixing of the first active material and the at least one second active material to form a mixed active material; a cap positioned over the membrane for sealing the reservoir such that removal of the cap results in controlled release of the AI from the mixed active material through the membrane.

22 Claims, 22 Drawing Sheets

(56) References Cited

U.S. PATENT DOCUMENTS

Figure 1A:
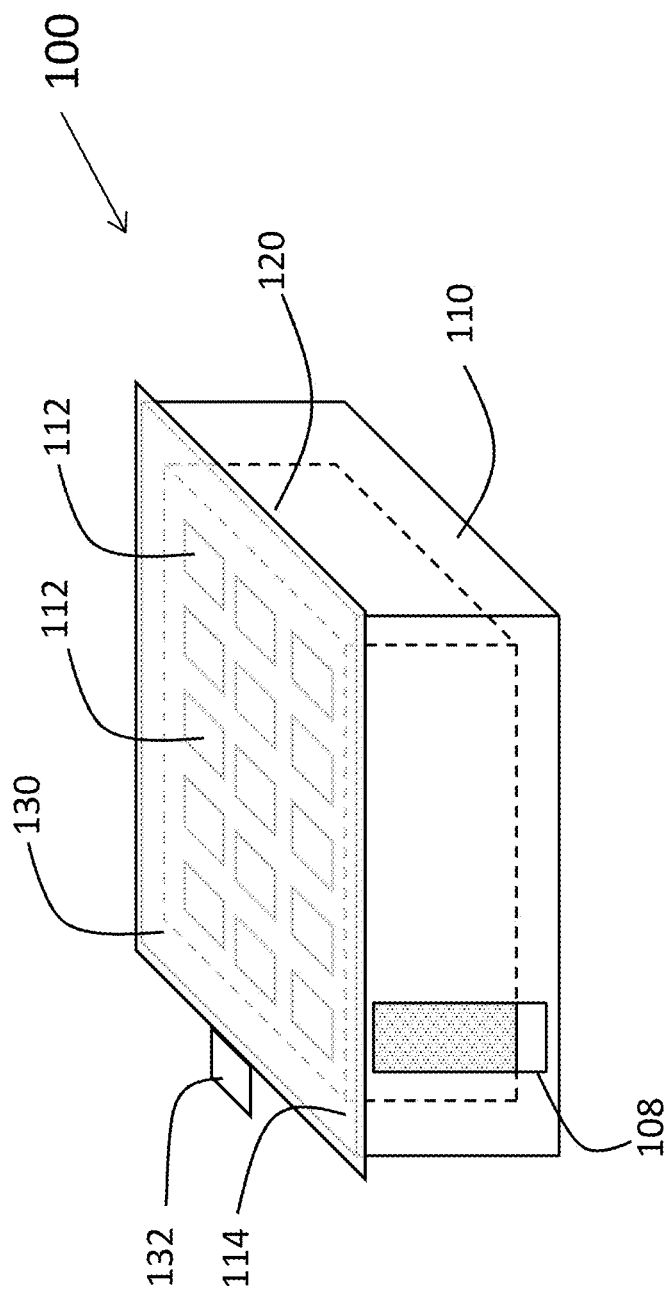

| | | | |
|---|---|---|---|
| 8,617,143 B2 | 12/2013 | Bachman et al. | |
| 8,677,679 B2* | 3/2014 | Black | A01M 1/2033 43/123 |
| 2001/0030243 A1* | 10/2001 | Hurry | A61L 9/12 239/60 |
| 2007/0194144 A1* | 8/2007 | Davis | A61L 9/03 239/34 |
| 2012/0312706 A1* | 12/2012 | Isaac | B65D 81/32 206/222 |
| 2013/0306498 A1* | 11/2013 | Azani | B65D 35/22 206/219 |
| 2017/0188581 A1 | 7/2017 | Decor et al. | |
| 2017/0340765 A1* | 11/2017 | Adair | B01F 3/04085 |
| 2018/0139960 A1* | 5/2018 | Sikuljak | A01N 25/34 |
| 2020/0164097 A1* | 5/2020 | Do | A61L 9/013 |

OTHER PUBLICATIONS

Wired (Year: 2014).*

Elman, N. M., et al. "Electro-thermally induced structural failure actuator (ETISFA) for implantable controlled drug delivery devices based on Micro-Electro-Mechanical-Systems." Lab on a Chip 10.20 pp. 2796-280. (2010).

Stevenson, Jennifer C., et al. "Controlled release spatial repellent devices (CRDs) as novel tools against malaria transmission: a semi-field study in Macha, Zambia." Malaria journal 17.1 437. (2018).

Bernier, Ulrich, et al. "Combined Experimental-Computational Approach for Spatial Protection Efficacy Assessment of Controlled Release Devices against Mosquitoes (*Anopheles*)," PLoS Negl Trop Dis. 211;13(3). (2019).

* cited by examiner

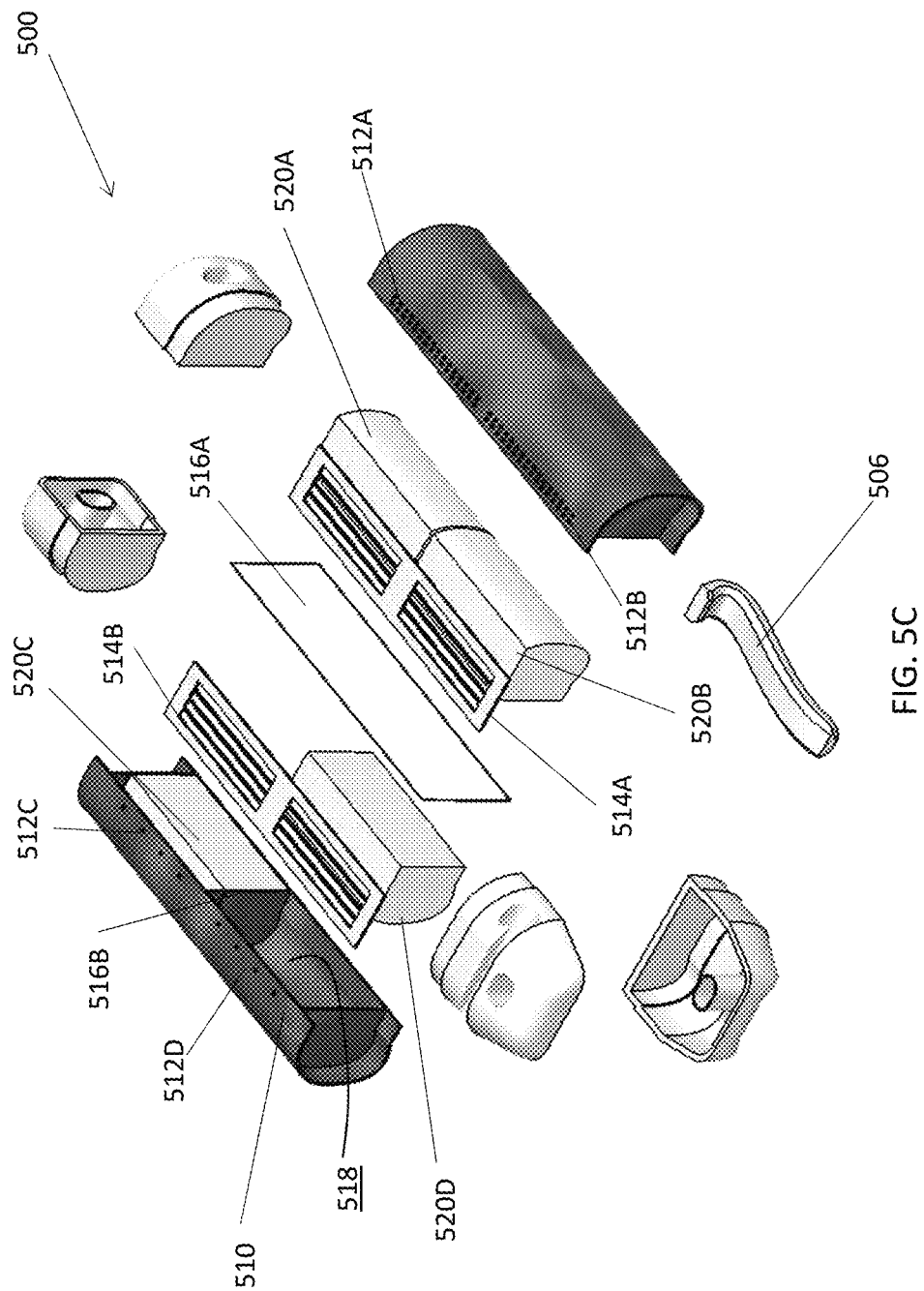

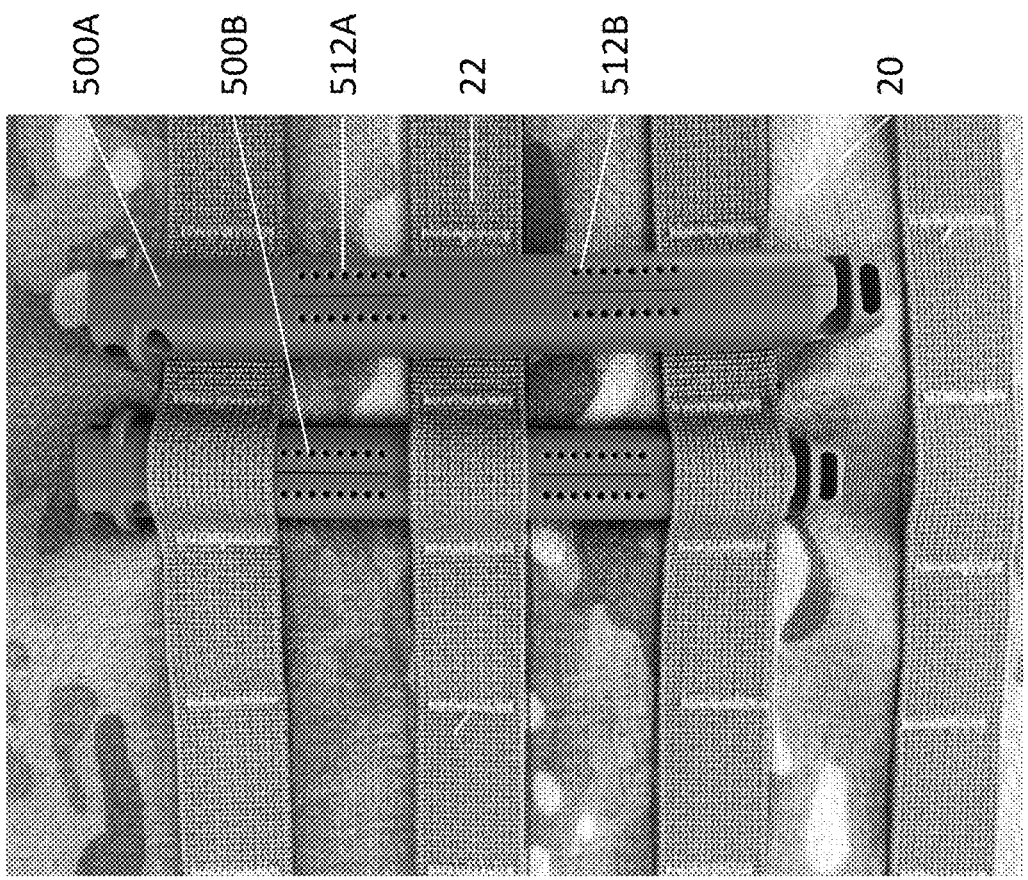

DEVICES AND METHODS FOR CONTROLLED RELEASE OF SUBSTANCES

CROSS REFERENCE TO RELATED APPLICATIONS

This application is a 371 application from international patent application PCT/IB2019/052121 filed Mar. 15, 2019, and is related to and claims the benefit of priority from U.S. Provisional patent application 62/643,769 filed Mar. 16, 2018, which is incorporated herein by reference in its entirety.

FIELD

Embodiments disclosed herein relate to devices and systems for controlled release of active ingredients (AI) into a fluid environment.

BACKGROUND

The problem of delivering AIs in a controlled release manner is known and has been addressed in the past in various ways such as controlled release devices (CRD) for vector control in agricultural, military, or civilian applications.

An example showing efficacy of CRDs is given in Stevenson, Jennifer C., et al. "Controlled release spatial repellent devices (CRDs) as novel tools against malaria transmission: a semi-field study in Macha, Zambia." Malaria journal 17.1 (2018): 437. Another example of CRD implementation is given in Bernier, Ulrich, et al. "Combined Experimental-Computational Approach for Spatial Protection Efficacy Assessment of Controlled Release Devices against Mosquitoes (*Anopheles*)," PLoS Negl Trop Dis. 2019 Mar. 11; 13(3).

The challenges facing development of effective CRDs include: controlling the release rate of the AI from within the CRD, and preventing activation or combination of the AI and other components within the CRD until the CRD is deployed. Further, there is a need to deliver CRDs that are inexpensive, environmentally friendly, and easy to manufacture and assemble.

SUMMARY

Exemplary embodiments disclosed herein relate to a device, system and method for controlled release of an active ingredient by active or passive mechanisms. Some exemplary embodiments provide for CRDs with multiple mechanisms for controlling the release rate of an AI from within the CRD and also mechanisms for preventing activation or combination of the AI and other components within the CRD until the CRD is deployed.

In some exemplary embodiments, the devices can be implemented as wearable devices for protection against vectors such as mosquitoes and ticks. In some exemplary embodiments, the devices can be deployed for applications such as: households for indoor or outdoor use; agricultural applications, for example to protect against multiple vectors that affect crops, such as weevils, or psyllids by attachment to a tree or deployment in soil; weed eradication such as use of herbicides provided in low dosage, low toxicity deliveries; floating devices to disperse larvicides to remove larvae from water; and so forth. In some exemplary embodiments, a device is manufactured from biodegradable, environmentally friendly materials.

In exemplary embodiments, a controlled release device (CRD) comprises: a reservoir wherein the reservoir is divided into a plurality of chambers; a first active material placed in a first chamber of the plurality of chambers and at least one second active material placed in at least one other of the plurality of chambers wherein the first active material comprises an active ingredient (AI), wherein the at least one second active material comprises one or both of a matrix and an altering material; a permeable membrane covering the first chamber; partitions positioned between adjacent chambers of the plurality of chambers for dividing the reservoir into chambers such that full or partial removal of one or more of the partitions results in mixing of the first active material and the at least one second active material to form a mixed active material; and a cap positioned over the membrane for sealing the reservoir such that removal of the cap results in controlled release of the AI from the mixed active material through the membrane.

In exemplary embodiments, the AI is one of transfluthrin or metofluthrin and the altering material of the at least one second active material is a volatile organic solvent such that the mixed active material is volatized transfluthrin.

In exemplary embodiments, the AI is one of transfluthrin or metofluthrin and the altering material of a first of at least one second active material is a volatile organic solvent and the altering material of a second of at least one second active material is DMSO such that the mixed active material is volatized transfluthrin or metofluthrin enhanced by DMSO.

In exemplary embodiments, the AI is one of transfluthrin or metofluthrin and the first active material further comprises DMSO for enhancing the transfluthrin wherein the altering material of the at least one second active material is a volatile organic solvent such that the mixed active material is volatized transfluthrin or metofluthrin enhanced by DMSO.

In exemplary embodiments, the volatile organic solvent is one of isopropanol, ethanol, methanol, or hexane. In exemplary embodiments, the AI is provided in a concentration of between 20%-95% of the mixed active material.

In exemplary embodiments, the altering material of a first of the at least one second active material is an exothermic reactant such that the mixed active material is the AI at an increased temperature.

In exemplary embodiments, the AI is transfluthrin and the altering material of a first of at least one second active material is a volatile organic solvent and the altering material of a second of at least one second active material is an exothermic reactant such that the mixed active material is volatized transfluthrin that is further volatized by increased temperature caused by the exothermic reactant.

In exemplary embodiments, the exothermic reactant is provided in the form of powder or rods selected from the group consisting of: iron, iron-based compounds, vermiculate (hydrated magnesium aluminum silicate), charcoal powder, and sodium chloride. In exemplary embodiments, the exothermic reactant is an exothermic reactant that is activated when exposed to oxygen such that the exothermic reactant is activated when the cap is removed.

In exemplary embodiments, the AI is one of an insecticide, a spatial repellent, a herbicide or a larvicide. In exemplary embodiments, the at least one second active material comprises an AI.

In exemplary embodiments, the cap is attached to the partitions such that removal of the cap results in removal of the partitions for mixing of the first active material and the at least one second active material to form a mixed active material.

In exemplary embodiments, the device of is adapted for sequential mixing of the first active material and the at least one second active material before release of the mixed active material wherein the adaptation comprises the cap can only be removed after the partitions are removed.

In exemplary embodiments, the first active material further comprises one or both of a matrix and an altering material.

In exemplary embodiments, the controlled release is determined by a controlled release mechanism selected from the group consisting of: changing the evaporation rate of the AI, changing the surface area of the matrix, changing the permeability of the membrane, adding one or more diffusion barriers, changing the viscosity of the first active material, changing the type of matrix, changing the temperature of the reservoir, utilizing an active release mechanism, changing the formulation of the first active material, changing the formulation of the at least one second active material, changing the permeability of the plurality of partitions, and a combination thereof.

In exemplary embodiments, the AI is selected from the group consisting of: a spatial repellent, an essential oil, a pyrethroid, an insecticide, an organochloride, an organophosphate, a carbamate, a neonicotinoid, a herbicide, an attractant, a larvicide, and a combination thereof.

In exemplary embodiments, the altering material is selected from the group consisting of: a solvent, an encapsulator, an enhancer, an exothermic reactant, an oil and a combination thereof.

In exemplary embodiments, the matrix is selected from the group consisting of: a porous material, a material with a high surface to volume ratio, a synthetic material, a material reactive to the altering material, and a combination thereof.

In exemplary embodiments, the device further comprises at least one diffusion barrier. In exemplary embodiments, the diffusion barrier comprises at least one hydrophobic domain.

In exemplary embodiments, a cap release mechanism is selected from the group consisting of: a mechanical cap release mechanism, a breakable cap release mechanism, an electrothermal rupture release mechanism, an electro-thermal-stress rupture release mechanism, an ultrasound cap release mechanism, a pH-based cap release mechanism, an optical-based release mechanism, and a combination thereof.

In exemplary embodiments, the device is adapted to be wearable. In exemplary embodiments, the device further comprises a buoyancy mechanism comprising an air chamber and a stabilizer for deployment of the device in a liquid. In exemplary embodiments, the device further comprises a parachute connected to the cap such that release of the CRD from a flying platform will result in opening of the parachute to thereby pull open the cap such that the AI is released.

In exemplary embodiments, the device further comprises an indicator for showing the amount of AI remaining in the device wherein the indicator comprises a scale and a dye calibrated to have the same volatility as the mixed active material to thus show the remaining concentration of AI in the device.

In exemplary embodiments, a controlled release device for controlled release of an AI in a liquid comprises: a reservoir; a first active material positioned in the reservoir wherein the first active material comprises the active ingredient (AI), wherein the AI is one of an insecticide, a spatial repellent, a herbicide or a larvicide; and a buoyancy mechanism comprising an air chamber and a stabilizer.

In exemplary embodiments, the device comprises a super hydro/oleic-phobic material outer layer.

In exemplary embodiments, a CRD for deployment from a flying platform comprises: a reservoir; a first active material positioned in the reservoir wherein the first active material comprises an active ingredient (AI), wherein the AI is one of an insecticide, a spatial repellent, a herbicide or a larvicide; and a parachute connected to a cap covering pores of the reservoir such that release of the CRD from a flying platform will result in opening of the parachute to thereby pull open the cap to thereby expose the pores such that AI is released.

In exemplary embodiments, a CRD comprises; a reservoir divided into a plurality of chambers; a plurality of active materials each placed in one of the plurality of chambers wherein each of the plurality of active materials comprises an AI, wherein the AI is one of an insecticide, a spatial repellent, a herbicide or a larvicide; and pores from each of the plurality of chambers for release of the AI from each of the plurality of active materials through the pores.

In exemplary embodiments, the pores are positioned so as to be exposed when the CRD is inserted into periodically spaced weavings of a vest. In exemplary embodiments, the vest is a US military standard vest.

In exemplary embodiments, the number of the pores corresponding to each of the plurality of chambers are adapted to change the release rate of the AI from the corresponding chamber. In exemplary embodiments, the size of the pores corresponding to each of the plurality of chambers is adapted to change the release rate of the AI from the corresponding chamber. In exemplary embodiments, the percentage concentration of the AI in each of the plurality of chambers is adapted to change the release rate of the AI from the corresponding chamber.

In exemplary embodiments, the CRD is adapted to be wearable. In exemplary embodiments, the CRD further comprises an indicator for showing the amount of AI remaining in each of the plurality of chambers of the device wherein the indicator comprises a scale and a dye calibrated to have the same volatility as the active material in each of the plurality of chambers to thus show the remaining concentration of AI in each of the plurality of chambers.

In exemplary embodiments, there are provided methods for integrating an AI with a high melting point into a matrix comprising: warming the AI to its liquid form; soaking the matrix with the liquid AI; and enabling cooling of the soaked matrix such that the AI solidifies integrated into the matrix.

In an exemplary method embodiment, the AI is transfluthrin. In an exemplary method embodiment the cooling is active cooling or passive cooling.

In exemplary embodiments, there are provided methods for integrating an AI with a high melting point into a matrix comprising: combining the AI with a solvent to liquefy the AI; soaking the matrix with the liquid AI-solvent mixture; and enabling evaporation of the solvent such that the AI solidifies integrated into the matrix. In an exemplary method embodiment the AI is transfluthrin.

In exemplary embodiments, a controlled release device comprises: a reservoir; a first active material positioned in the reservoir wherein the first active material comprises an active ingredient (AI) wherein the AI is one of an insecticide, a spatial repellent, a herbicide or a larvicide; a permeable membrane covering the reservoir; and a cap positioned over the membrane for sealing the reservoir such that removal of the cap results in controlled release of the AI from the first active material through the membrane.

In exemplary embodiments, the first active material further comprises one or both of a matrix and an altering material.

In exemplary embodiments, the controlled release is determined by a controlled release mechanism selected from the group consisting of: changing the evaporation rate of the first active material, changing the surface area of the matrix, changing the permeability of the membrane, adding one or more diffusion barriers, changing the viscosity of the first active material, changing the type of matrix, changing the temperature of the reservoir, utilizing an active release mechanism, changing the formulation of the first active material, and a combination thereof.

In exemplary embodiments, the AI is selected from the group consisting of: a spatial repellent, an essential oil, a pyrethroid, an insecticide, an organochloride, an organophosphate, a carbamate, a neonicotinoid, a herbicide, an attractant, a larvicide, and a combination thereof.

In exemplary embodiments, the altering material is selected from the group consisting of: a solvent, an encapsulator, an enhancer, an exothermic reactant, an oil and a combination thereof.

In exemplary embodiments, the matrix is selected from the group consisting of: a porous material, a material with a high surface to volume ratio, a synthetic material, a material reactive to the altering material, and a combination thereof.

In exemplary embodiments, the device further comprises at least one diffusion barrier. In exemplary embodiments, the diffusion barrier comprises at least one hydrophobic domain.

In exemplary embodiments, the cap hermetically seals the reservoir.

In exemplary embodiments, a cap release mechanism is selected from the group consisting of: a mechanical cap release mechanism, a breakable cap release mechanism, an electrothermal rupture release mechanism, an electro-thermal-stress rupture release mechanism, an ultrasound cap release mechanism, a pH-based cap release mechanism, an optical-based release mechanism, and a combination thereof.

In exemplary embodiments, the device is adapted to be wearable. In exemplary embodiments, the device comprises a buoyancy mechanism for deployment of the device in a liquid. In exemplary embodiments, the device is adapted for deployment from a flying platform and wherein the adaptation comprises a parachute. In exemplary embodiments, the reservoir is formed from a fold-up container.

In exemplary embodiments, the device further comprises an indicator for showing the amount of AI remaining in the device wherein the indicator comprises a scale and a dye calibrated to have the same volatility as the active material to thus show the remaining concentration of AI in the device.

Implementation of the method and system of the present invention involves performing or completing certain selected tasks or steps manually, automatically, or a combination thereof.

Unless otherwise defined, all technical and scientific terms used herein have the same meaning as commonly understood by one of ordinary skill in the art to which this invention belongs. The materials, methods, and examples provided herein are illustrative only and not intended to be limiting.

BRIEF DESCRIPTION OF THE DRAWINGS

Aspects, embodiments and features disclosed herein will become apparent from the following detailed description when considered in conjunction with the accompanying drawings. Like elements may be numbered with like numerals in different FIGS.:

FIG. 1A shows an exemplary embodiment of a CRD with a cap on;

FIG. 1B shows an exemplary embodiment of a CRD with a cap off;

FIG. 1C shows a sectional illustration of an exemplary embodiment of a CRD with a single chamber;

FIG. 1D, FIG. 1E and FIG. 1F show exemplary embodiments of a CRD with a diffusion barrier;

FIG. 2A and FIG. 2B show sectional illustrations of an exemplary embodiment of a CRD with two chambers;

FIG. 3A and FIG. 3B show sectional illustrations of an exemplary embodiment of a CRD with three chambers;

FIG. 4A and FIG. 4B show flowcharts of a process for integrating an AI with a high melting point into a matrix;

FIG. 5A, FIG. 5B, FIG. 5C, and FIG. 5D show alternate views and an exploded view of an exemplary embodiment of a CRD;

FIG. 5E shows a graph of exemplary dispersion rates for a CRD with multiple chambers;

FIG. 5F and FIG. 5G show photographs of an exemplary CRD adapted for attachment to clothing;

FIG. 6 shows an exemplary embodiment of a CRD for deployment into a fluid environment;

FIG. 7 shows an exemplary embodiment of a CRD for deployment from an flying platform; and FIG. 8A, FIG. 8B, FIG. 8C and FIG. 8D show an exemplary embodiment of a CRD formed from a fold-up reservoir.

DETAILED DESCRIPTION

Exemplary embodiments relate to a system, device and method for controlled release of an active ingredient (AI) from a reservoir into a fluid environment. In some exemplary embodiments, the reservoir is wearable. Exemplarily, the fluid environment is air. In exemplary embodiments, the AIs of the present disclosure serve for any one of spatial repellents, insecticides, herbicides, larvicides, or a combination of these. Optionally, the devices of the present disclosure serve for the release of AIs with other functions.

FIG. 1A shows an exemplary embodiment of a CRD with a cap on and FIG. 1B shows an exemplary embodiment of a CRD with a cap off. As shown, a reservoir 110 of a CRD 100 houses an active material 120. Active material 120 comprises an active ingredient 122 and other materials as further described herein. Reservoir 110 is covered by a permeable membrane 114. Membrane 114 comprises release pores 112 which are covered for preventing release of AI 120 by a sealing cap 130. Pores 112 are shown in FIGS. 1A-1B as rectangular, but may optionally be of any shape. Pores 112 are optionally sized so as to control the release kinetics of AI 122. Pores 112 are shown herein as visible openings but are optionally microscopic permeable paths through permeable membrane 114.

FIG. 1A shows sealing cap in position on reservoir 110 and FIG. 1B shows sealing cap 130 removed for release of AI 120 through pores 112. Cap 130 comprises a cap release mechanism 132 which is shown here as a pull tab for pulling off cap 130 where cap 130 is attached for example by an adhesive to reservoir 110. In some embodiments, cap 130 can be replaced onto reservoir 110 after being removed, to reseal reservoir 110. In other embodiments, cap 130 cannot be replaced onto reservoir 110 to reseal reservoir 110 after being removed.

Optionally, cap release mechanism 132 may be any one of:

- A mechanical cap release mechanism, where cap 130 is held onto reservoir by means known in the art such as a screw cap or pull cap;
- A breakable cap release mechanism, where cap 130 is adapted to be broken open by a user using mechanical force such as by having pre-scored sections;
- An electrothermal rupture release mechanism, such as published in Elman, N. M., et al. "Electro-thermally induced structural failure actuator (ETISFA) for implantable controlled drug delivery devices based on Micro-Electro-Mechanical-Systems." Lab on a Chip 10.20 (2010): 2796-2804, where cap 130 comprises a base material, for example, silicon nitride, and one or more planar fuses comprising, for example, titanium, gold, and/or copper, that are placed across the base material. Upon applying an electrical pulse with a given current, the fuses break and cap 130 then breaks open due to the thermo-electric reaction;
- An electro-thermal-stress rupture release mechanism, where cap 130 comprises a base material, for example silicon nitride, and one or more fuses comprising, for example, titanium, gold and/or copper, where fuses are positioned in the inner perimeter of cap 130 where typically (together with the center) the mechanical stress is at its highest. By applying a voltage to the fuses, the fuses act as resistors thereby dissipating heat which is transferred to cap 130, forcing cap 130 to expand beyond the yield strength of the base material, thereby breaking open cap 130;
- An ultrasound cap release mechanism, where sound waves are applied with enough energy to break cap 130 by matching the applied sound frequency to the resonant frequency of cap 130. Optionally, where more than one cap 130 is provided, each cap 130 is characterized by a different resonant frequency to enable selective breaking open of each cap 130. Optionally, additional structural features could be added to a cap, e.g. additional rectangular features to pre-define such changes in resonance frequencies without changing the lateral dimensions of cap 130;
- A pH-based cap release mechanism, where cap 130 comprises materials prone to react with a given environmental pH to degrade until the mechanical structure of cap 130 is fully compromised. In a non-limiting example, a device 100 for release of an AI 122 into water could rely on the water pH to chemically degrade cap 130;
- An optical-based release mechanism, where cap 130 is burst using optical energy such as a laser.

Cap 130, reservoir 110 and membrane 114 may be transparent, semi-transparent or opaque. Cap 130 and reservoir 110 are here shown as semi-transparent for clarity. In some exemplary embodiments, cap 112 hermetically seals reservoir 110. In some exemplary embodiments, reservoir 110 and cap 130 are formed of a non-porous material.

Figure 1B:
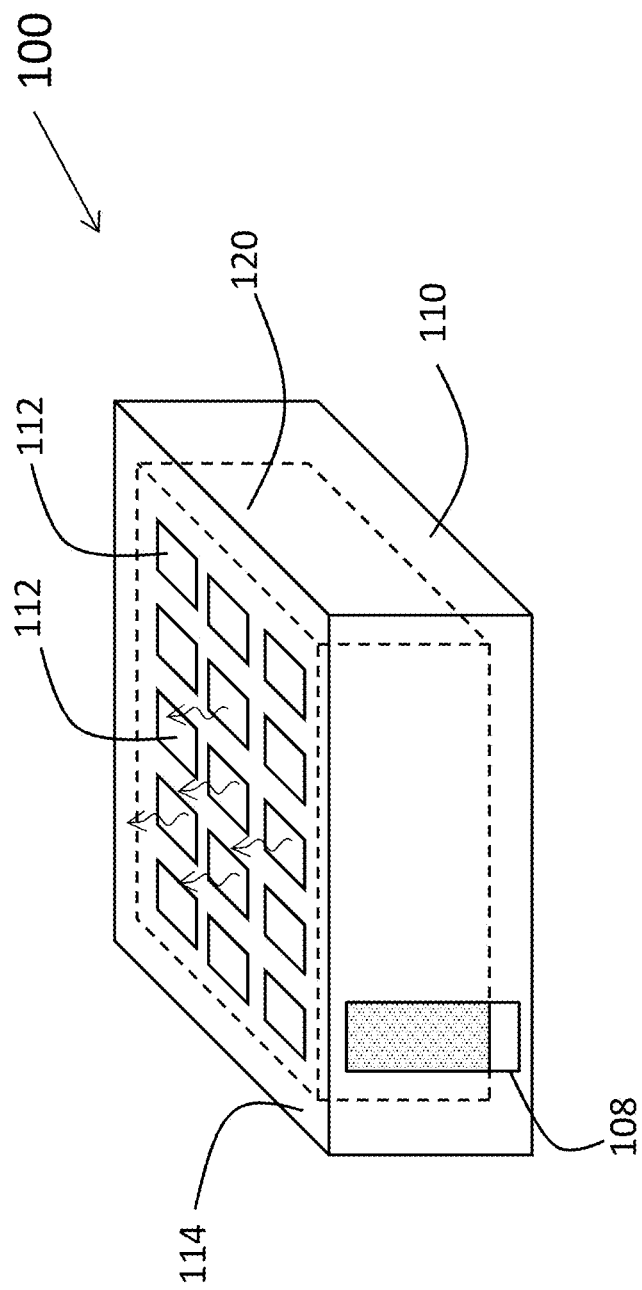
Figure 1C:
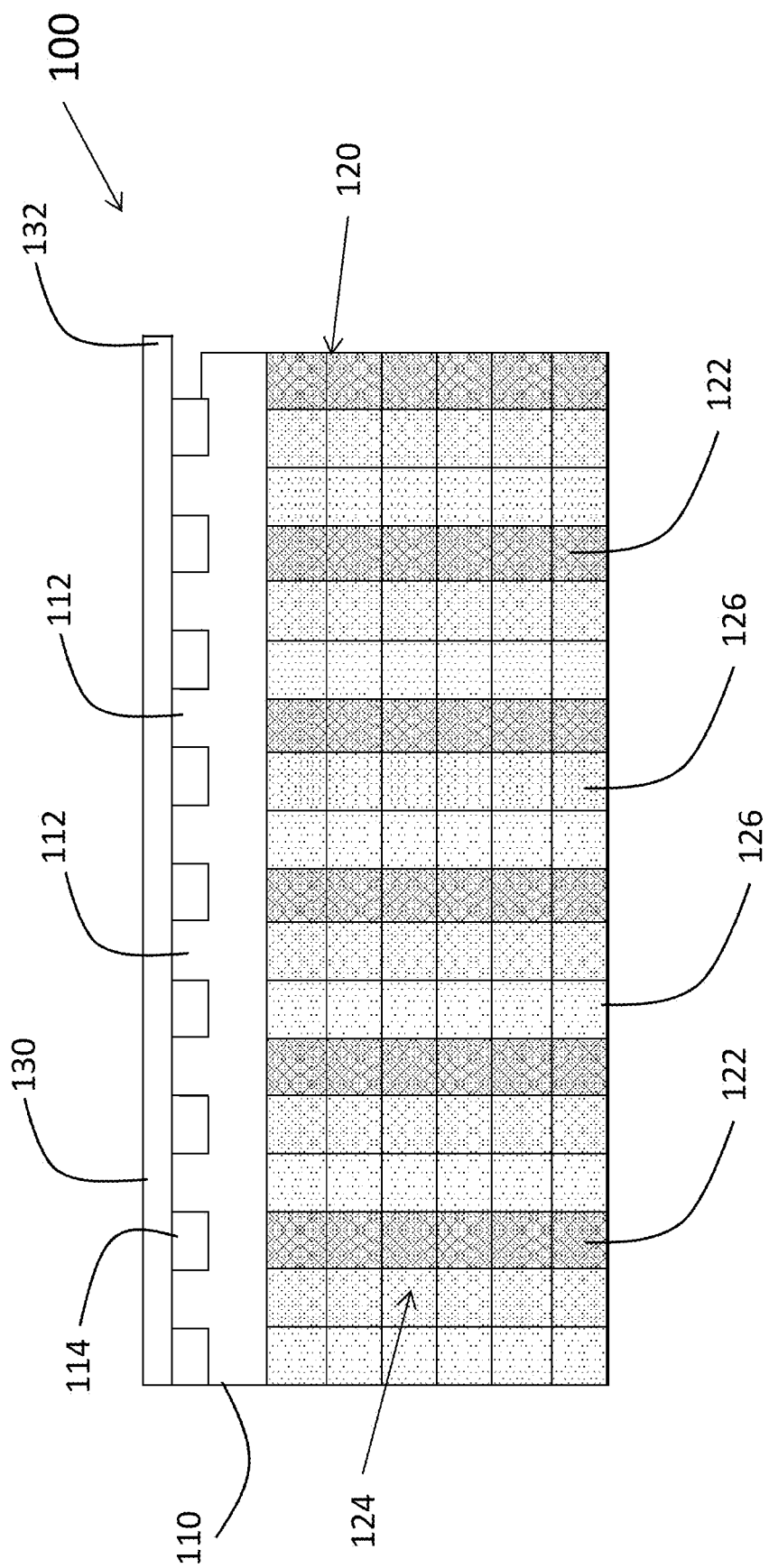
Figure 1D:
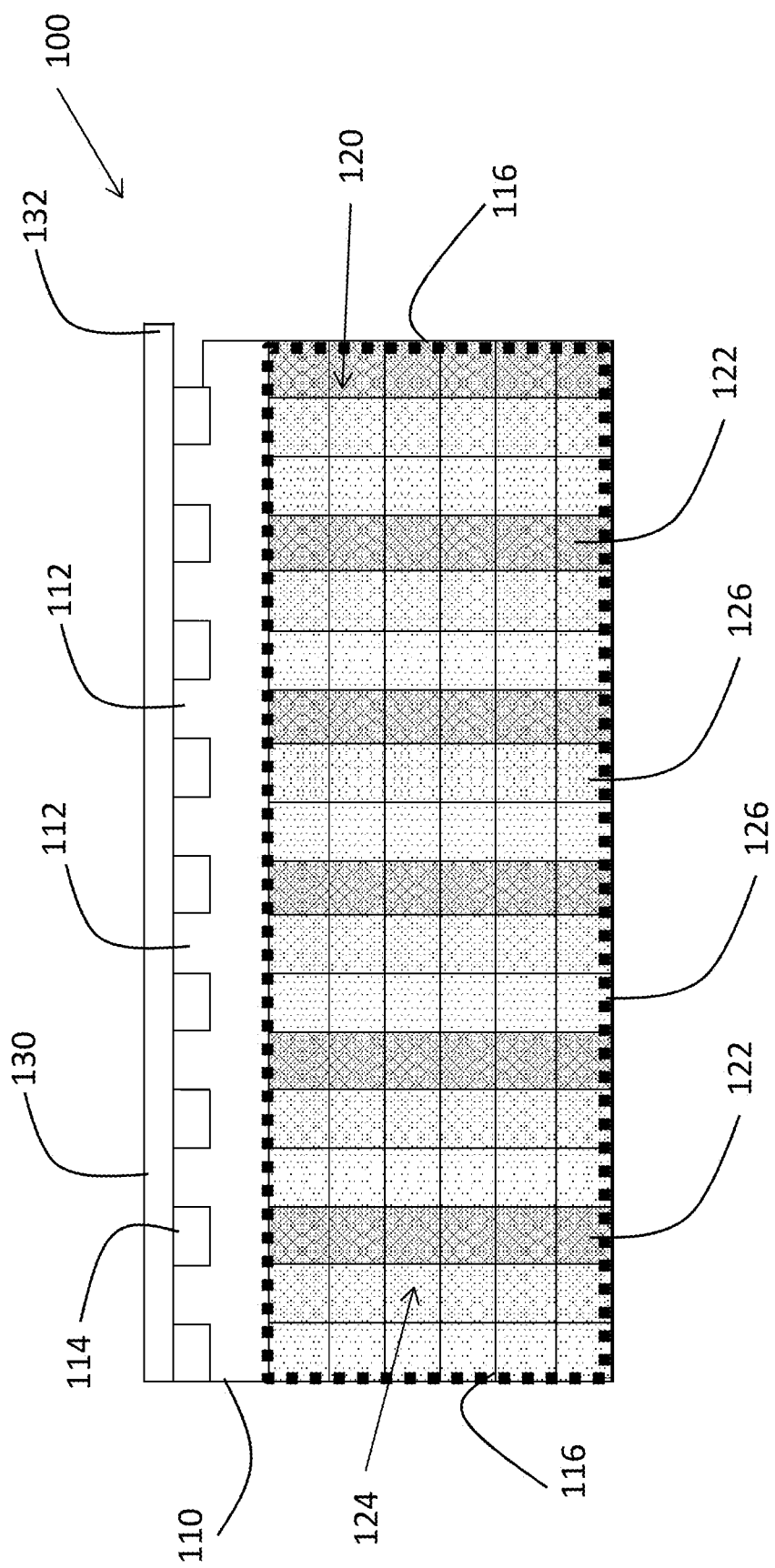
Figure 1F:
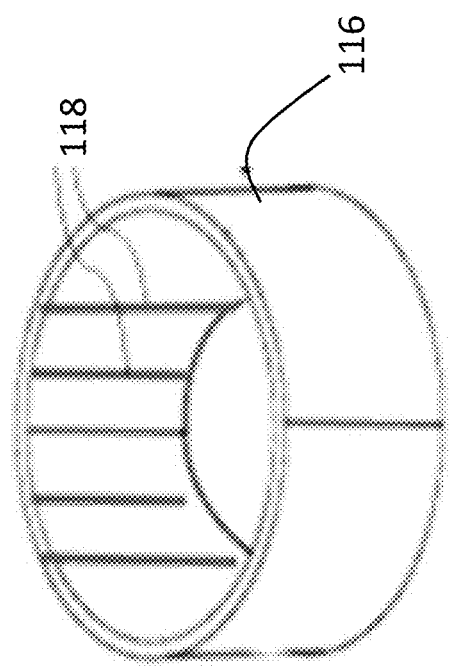
Figure 1E:
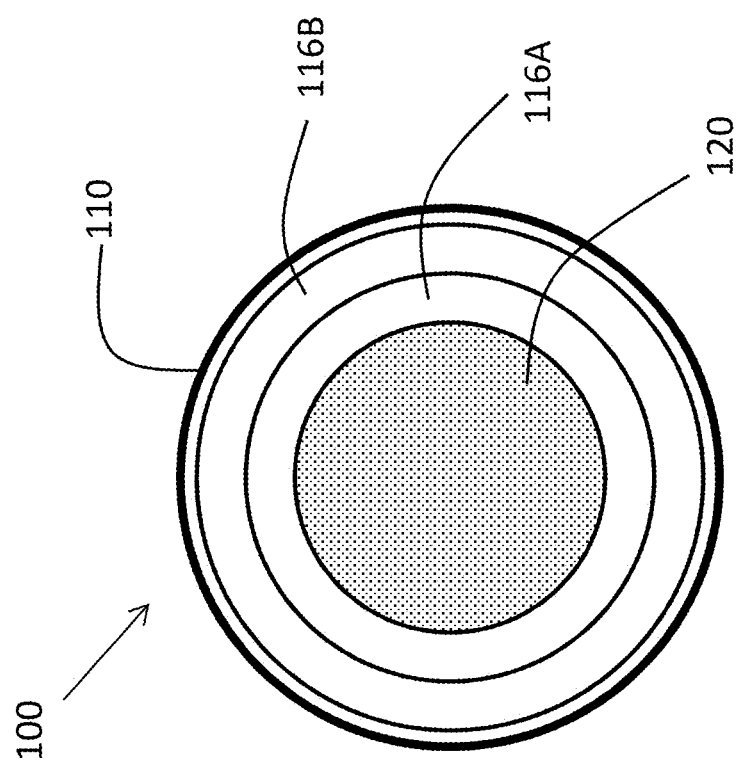
Figure 2A:
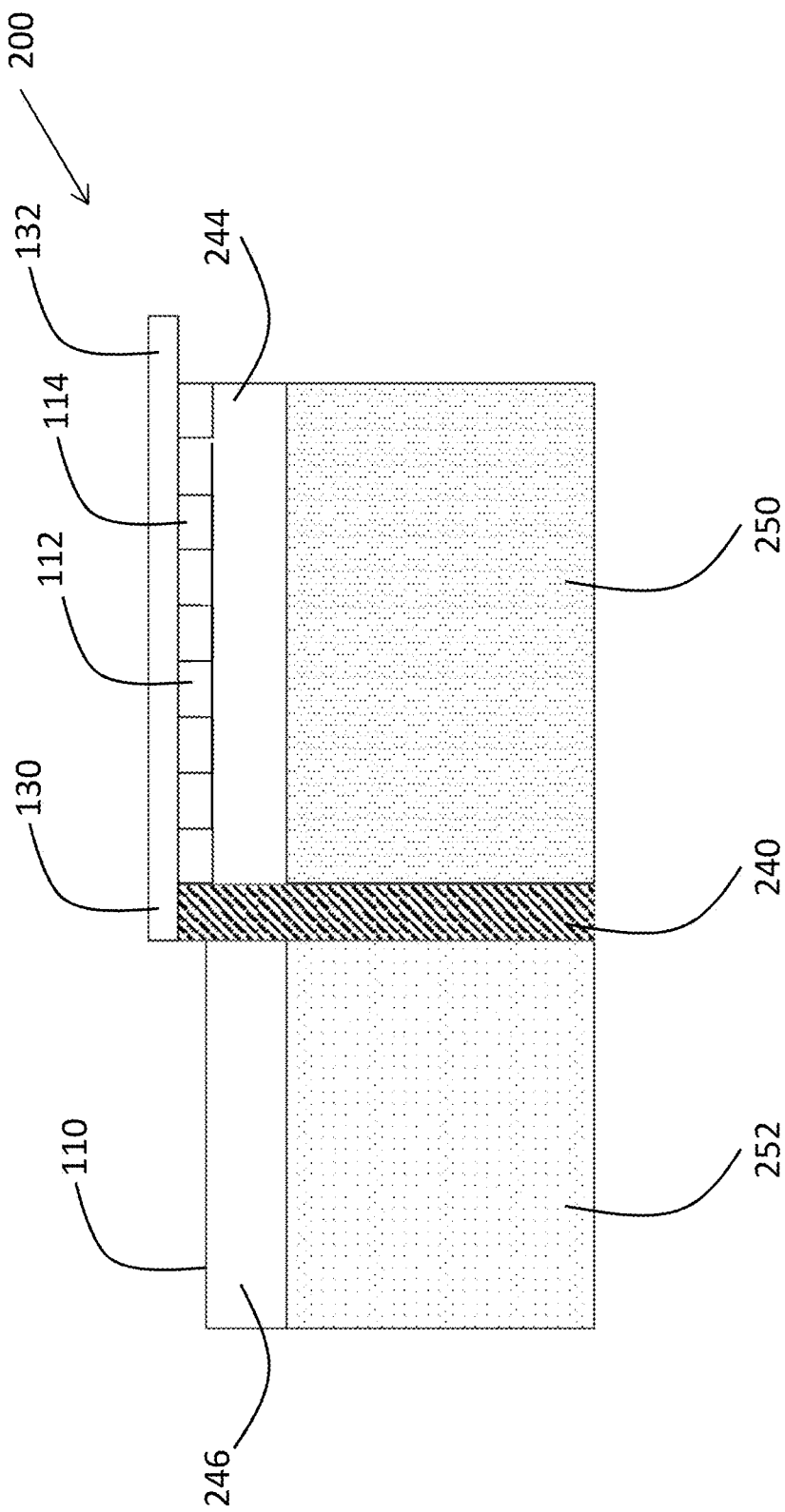
Figure 2B:
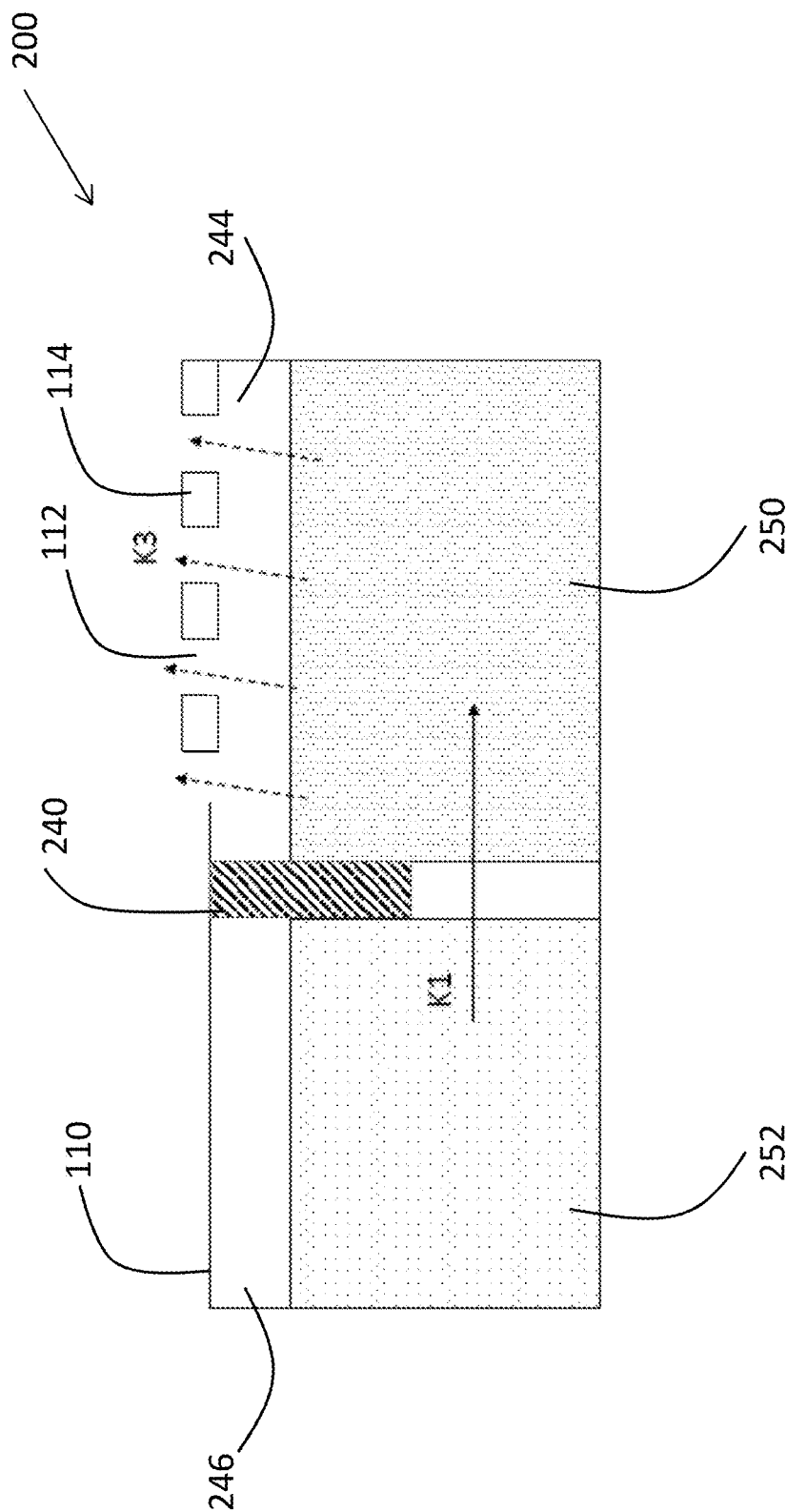
Figure 3A:
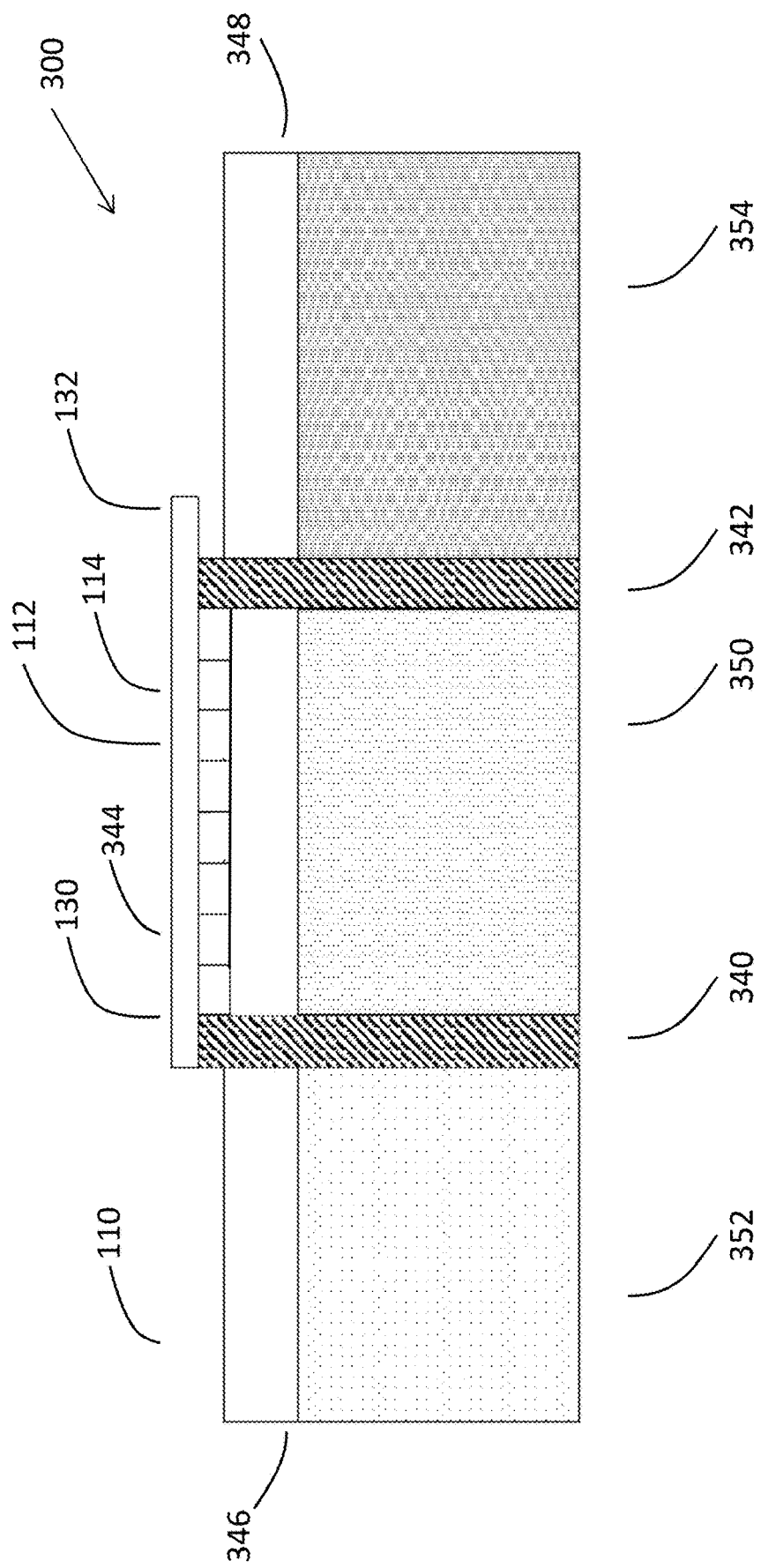
Figure 3B:
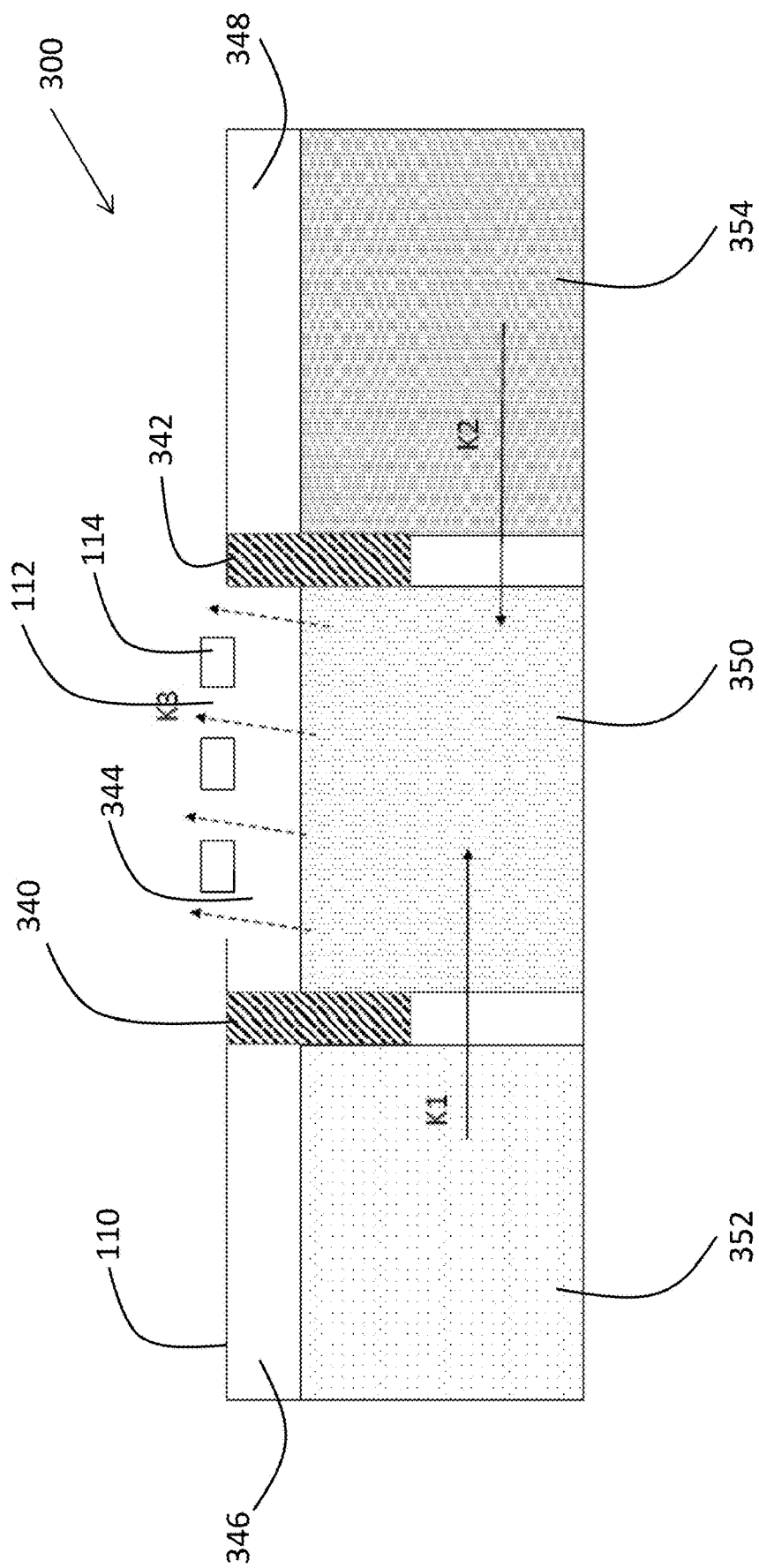

In the illustrative drawing of FIGS. 1A-1B, reservoir 110 is shown as having a rectangular form, but this should not be considered limiting and reservoir 110 and the active material 120 therein may optionally have any required shape such as shown in FIG. 1E (a top-down cross-sectional view of circular device 100).

FIG. 1C shows a sectional illustration of an exemplary embodiment of a CRD with a single chamber. Device 100 is provided with active material 120 comprising an AI 122, an optional matrix 124, and/or an optional altering material 126. Altering material 126 may comprise solvents, oils, enhancers, exothermic reactants, encapsulators, excipients, or a combination of these. It should be understood that where AI 122 is combined with altering materials 126, that device 100 may diffuse/release AI 122 as well as altering materials 126. CRD 100 optionally includes an indicator 108 showing the amount of AI 122 remaining in CRD 100. Indicator 108 is optionally a window into device 100 with a scale and a dye calibrated to have the same or similar volatility as the formulation of active material 120 to thus show the remaining concentration of AI 122.

FIG. 1C shows active material 120 comprising a matrix 124 having equally sized and spaced cells. It should be appreciated that matrix 124 as shown is illustrative, and that AI 122 and other materials will typically be mixed together at a molecular level and spread throughout matrix 124. The active material may be optionally provided in a gel form.

In the embodiment of FIGS. 1C-1E, reservoir 110 comprises a single chamber. In such an embodiment, where active material 120 comprises an already-mixed formulation, reservoir 110 is hermetically sealed by cap 130 so as to prevent release or activation of active material 120. Exemplary embodiments with more than one chamber are described below.

In some exemplary embodiments, matrix 124 comprises a porous (sponge) material, for example but not limited to cellulose. Matrix 124 holds AI 122 by absorption-adsorption mechanisms. Matrix 124 is optionally provided with a high surface to volume ratio for increasing the surface area for evaporation of AI 122. Matrix 124 optionally adsorbs/absorbs AI 122 for altering the release rate of AI 122. Matrix 124 optionally comprises a synthetic material such as but not limited to Polyurethane (ether & ester grades), Micro-Cellular Urethanes, Reticulated Polyurethane Foam Filters, Crosslink Polyethylene Roll Stock, Crosslink Polyethylene, and/or Polyurethane.

Optionally, matrix 124 is reactive to an altering material 126 such as a solvent, such that matrix 124 dissolves or is biodegraded at a given rate thereby releasing AI 122 contained therein. As a non-limiting example, a matrix 124 of cellulose sponge can react with an acetone solvent.

In some exemplary embodiments, AI 122 comprises a spatial repellent, insecticide, herbicide, larvicide, or a combination of these. AI 122 may be any one of, or a combination of, but is not limited to:

- Essential oils such as citronella, geraniol, lemon grass, peppermint, cedar oil, eugenol;
- A pyrethroid such as metofluthrin, transfluthrin, Allethrin, Bifenthrin, Cyhalothrin, Lambda-cyhalothrin, Cypermethrin, Cyfluthrin, Deltamethrin, Etofenprox, Fenvalerate, Permethrin, Phenothrin, Prallethrin, Resmethrin, Tetramethrin, Tralomethrin;
- An insecticide, such as imidacloprid, Heptachlor, Hexachlorobenzene, Lindane (gamma-hexachlorocyclohexane), Methoxychlor, Mirex, Pentachlorophenol, TDE;
- An organochloride, such as Aldrin, Chlordane, Chlordecone, DDT, Dieldrin, Endosulfan, Endrin;
- An organophosphate, such as Acephate, Azinphosmethyl, Bensulide, Chlorethoxyfos, Chlorpyrifos, Chlorpyriphos-methyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Mevinphos, Monocrotophos, Naled, Omethoate, Oxydemeton-methyl, Parathion, Parathion-methyl, Phorate, Phosalone, Phosmet, Phostebupirim, Phoxim, Pirimiphos-methyl, Profenofos, Terbufos, Tetrachlorvinphos, Tribufos, Trichlorfon;

A carbamate, such as Aldicarb, Bendiocarb, Carbofuran, Carbaryl, Dioxacarb, Fenobucarb, Fenoxycarb, Isoprocarb, Methomyl, 2-(1-Methylpropyl)phenyl methylcarbamate;

A neonicotinoid, such as Acetamiprid, Clothianidin, Imidacloprid, Nitenpyram, Nithiazine, Thiacloprid, Thiamethoxam, Anabasine, Anethole, Annoninm *Asimina* for lice, Azadirachtin, Caffeine, Carapa, Cinnamaldehyde, Cinnamon leaf oil, Cinnamyl acetate, Deguelin, Derris, *Desmodium caudatum*, Eugenol, Linalool, Myristicin, Neem (Azadirachtin), *Nicotiana rustica* (nicotine), *Peganum harmala*, seeds (smoke from), root, Oregano oil, Polyketide, *Pyrethrum, Quassia*, Tetranortriterpenoid, Thymol.

A herbicide, such as glycphosates and/or paraquat, and/or

A larvicide, such as *Bacillus thuringiensis israelensis* (BTI).

Figure 4A:
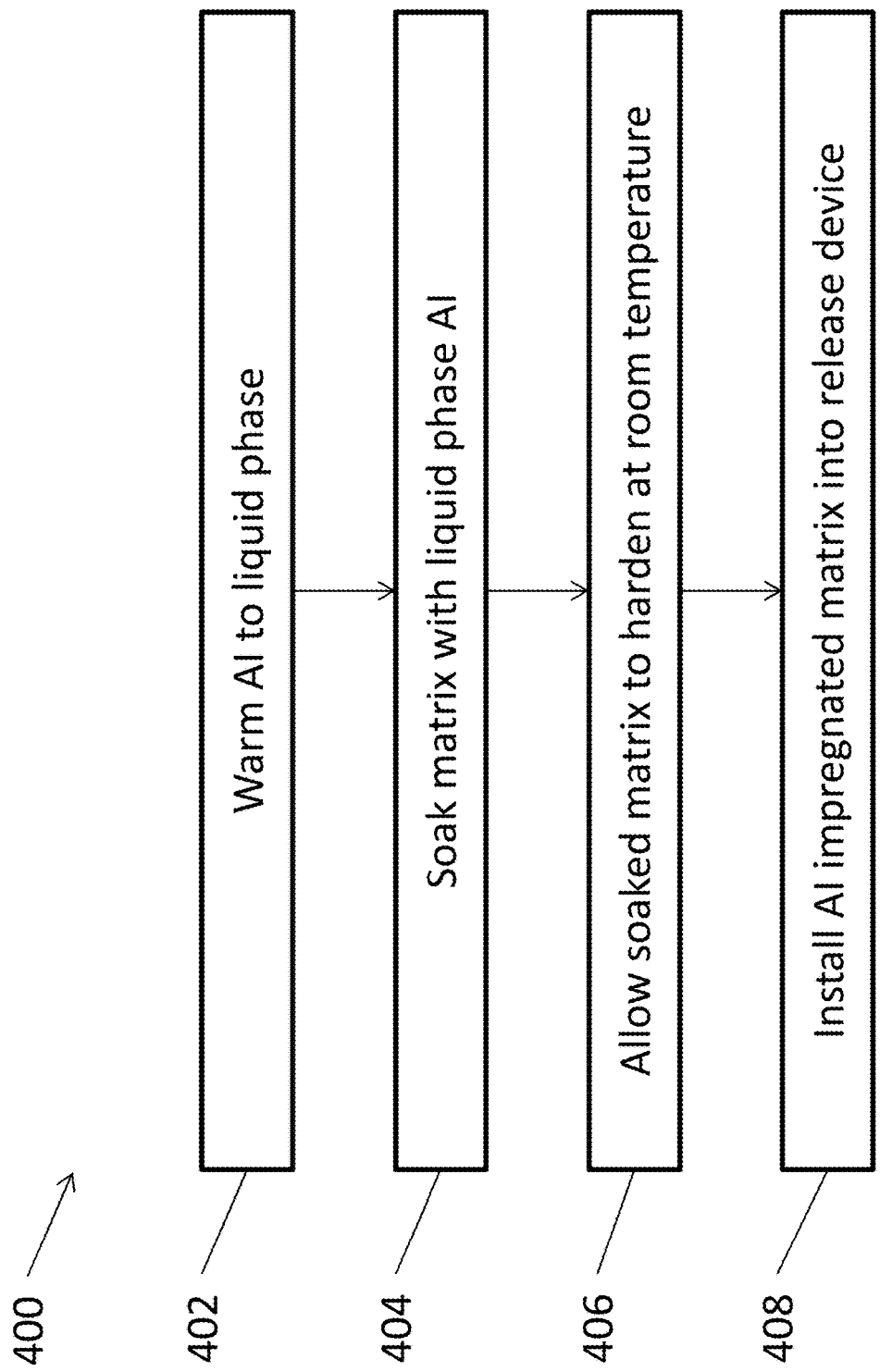
Figure 4B:
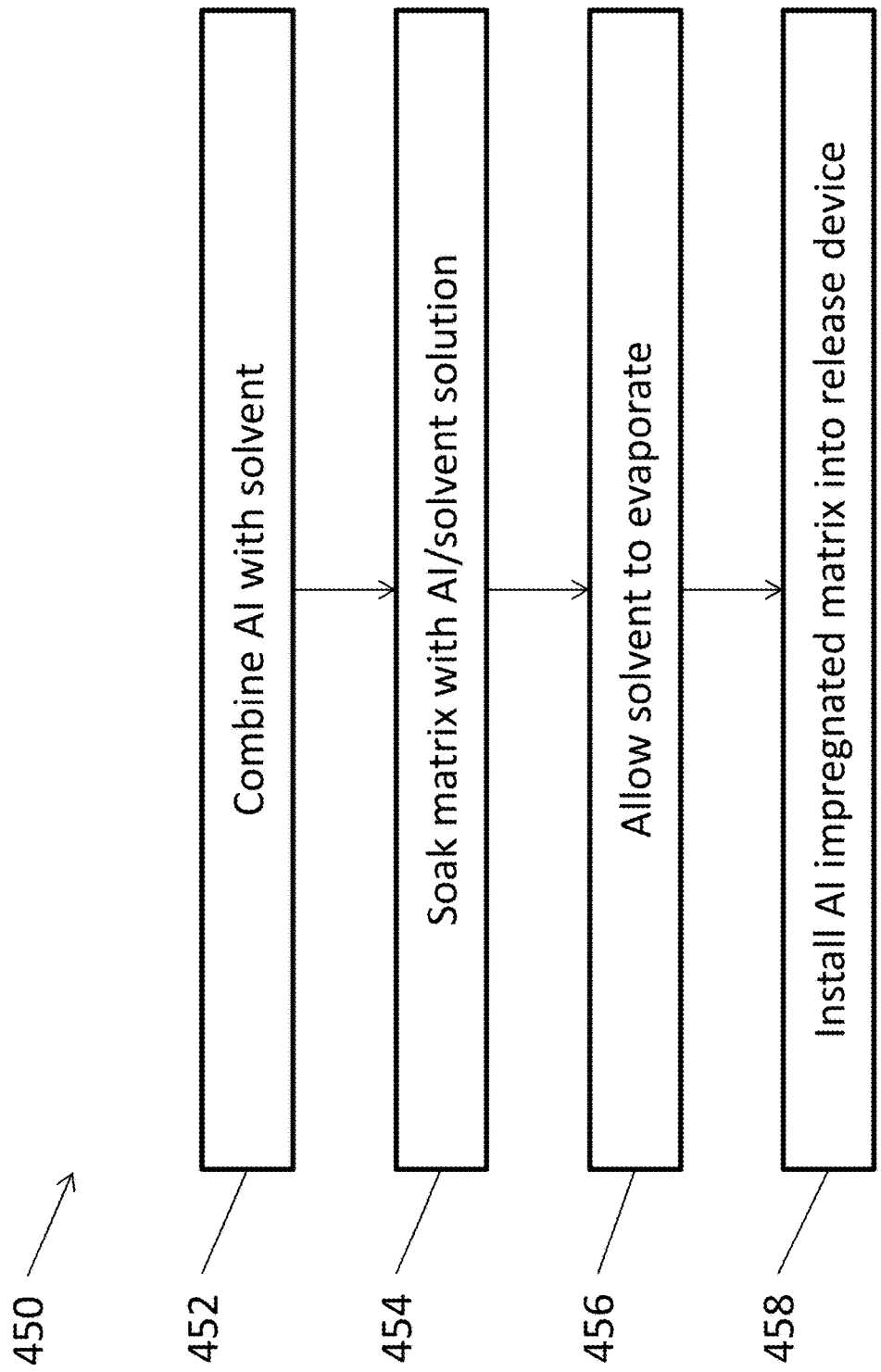
Figure 5A:
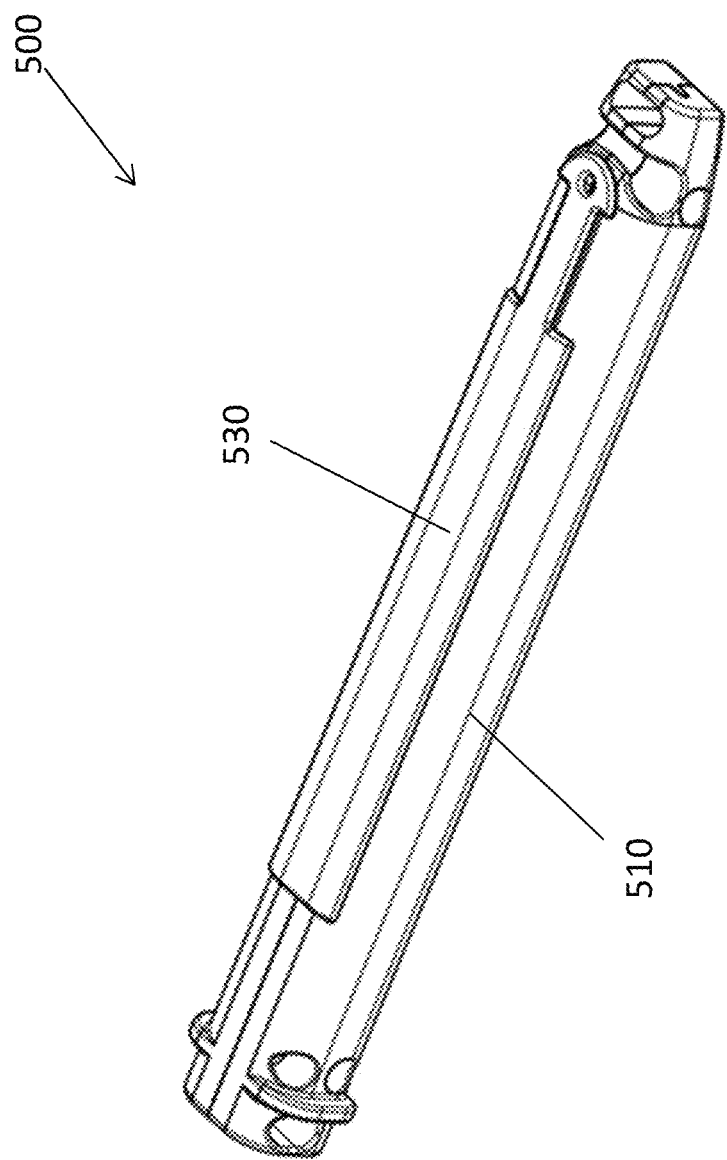
Figure 5B:
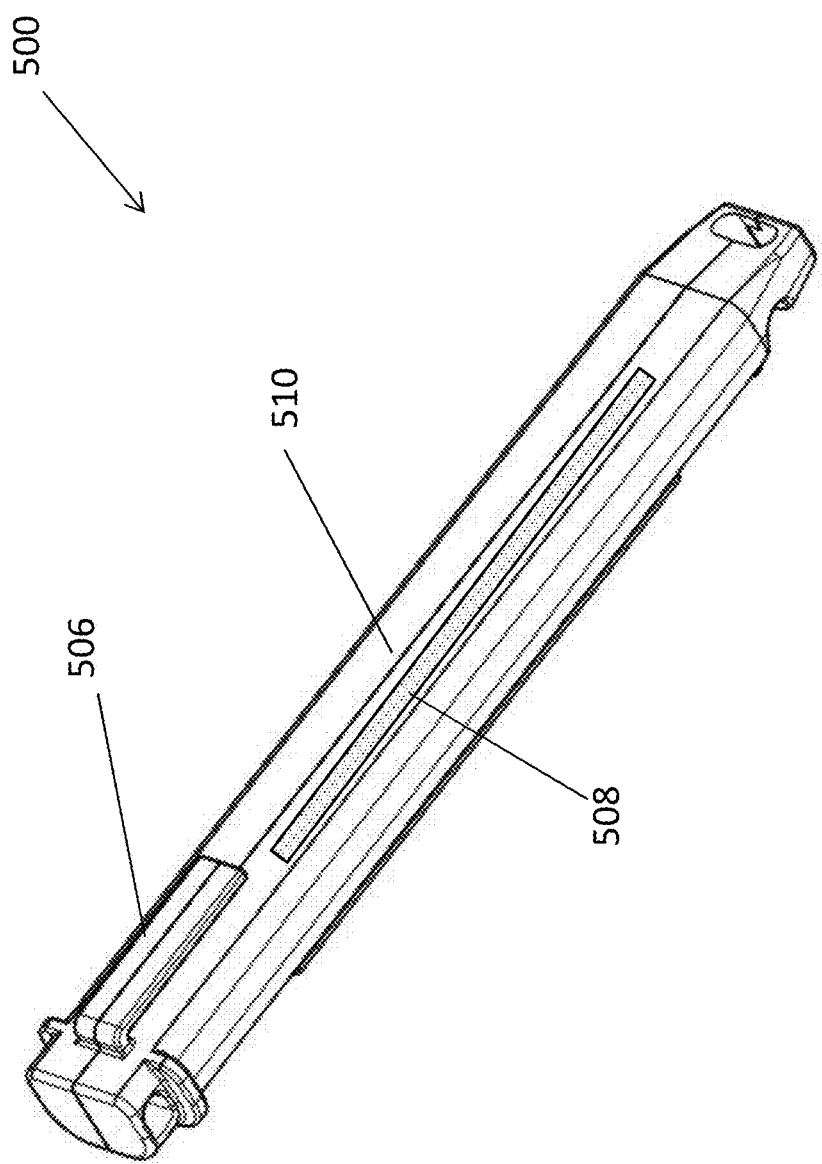
Figure 5D:
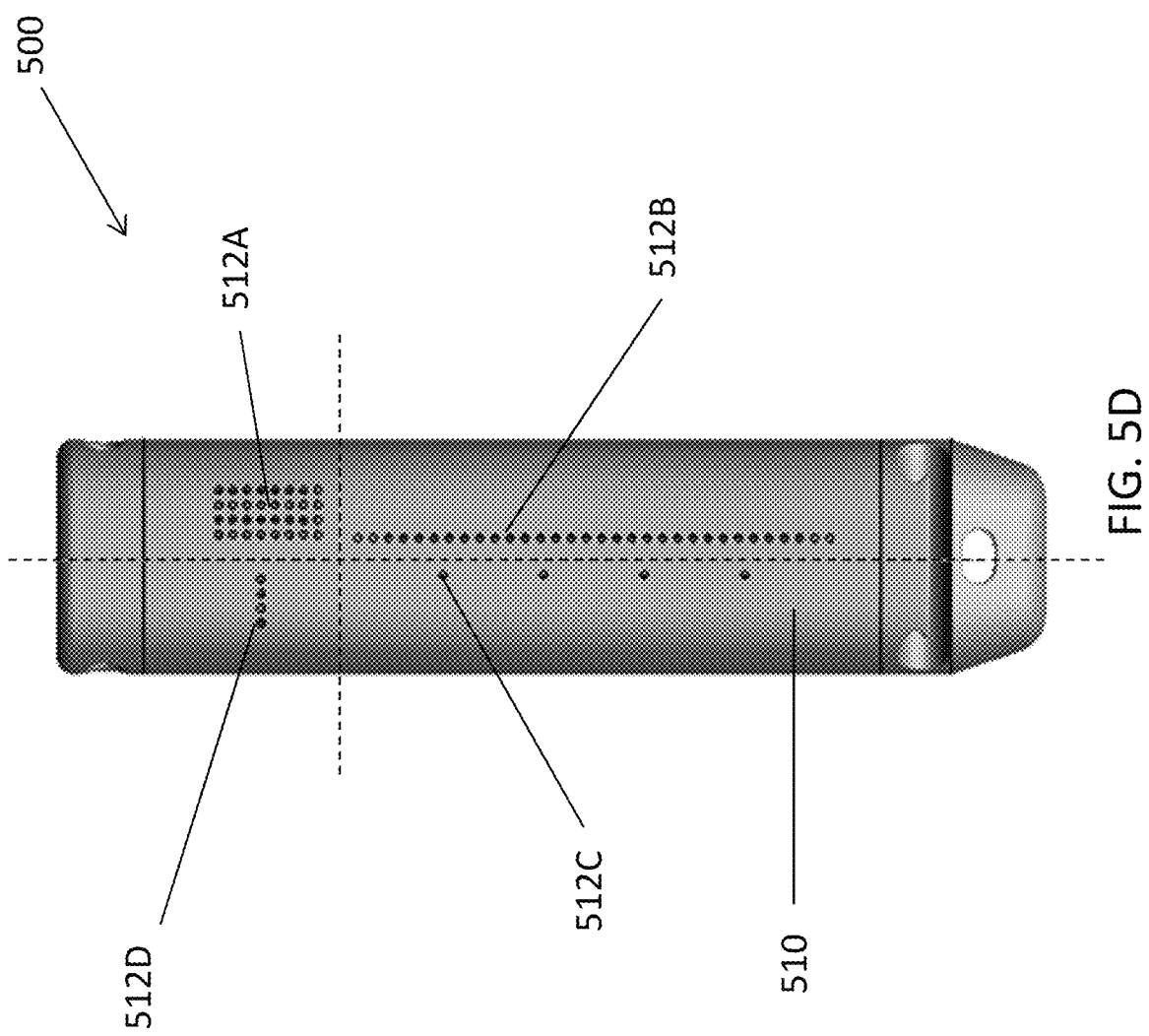
Figure 5E:
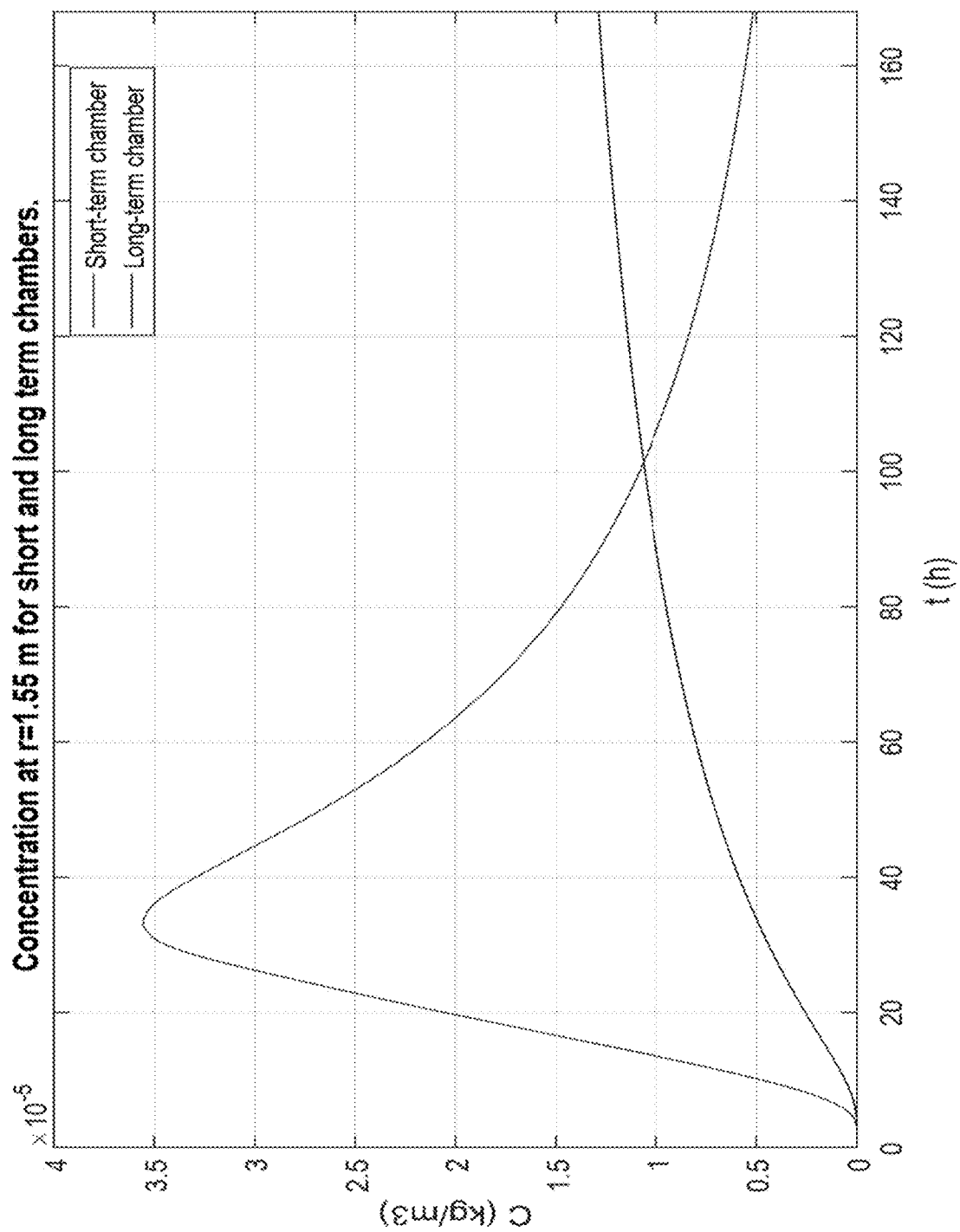
Figure 5G:
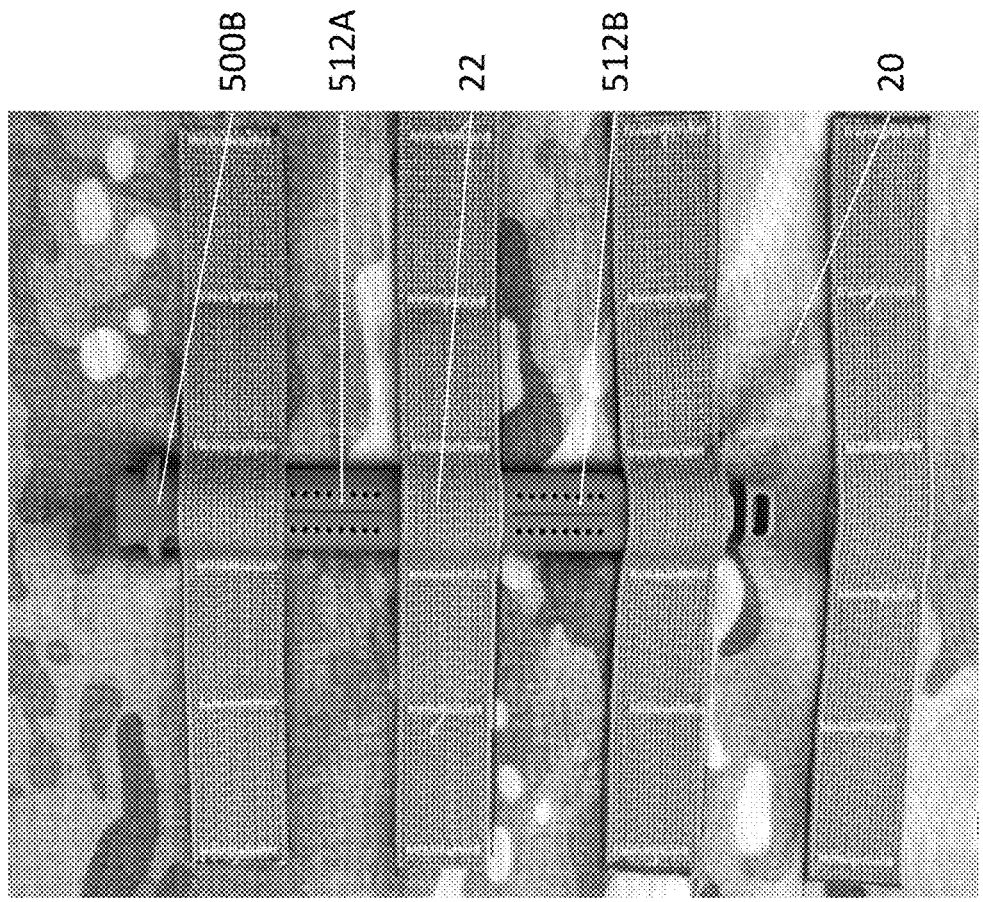
Figure 6:
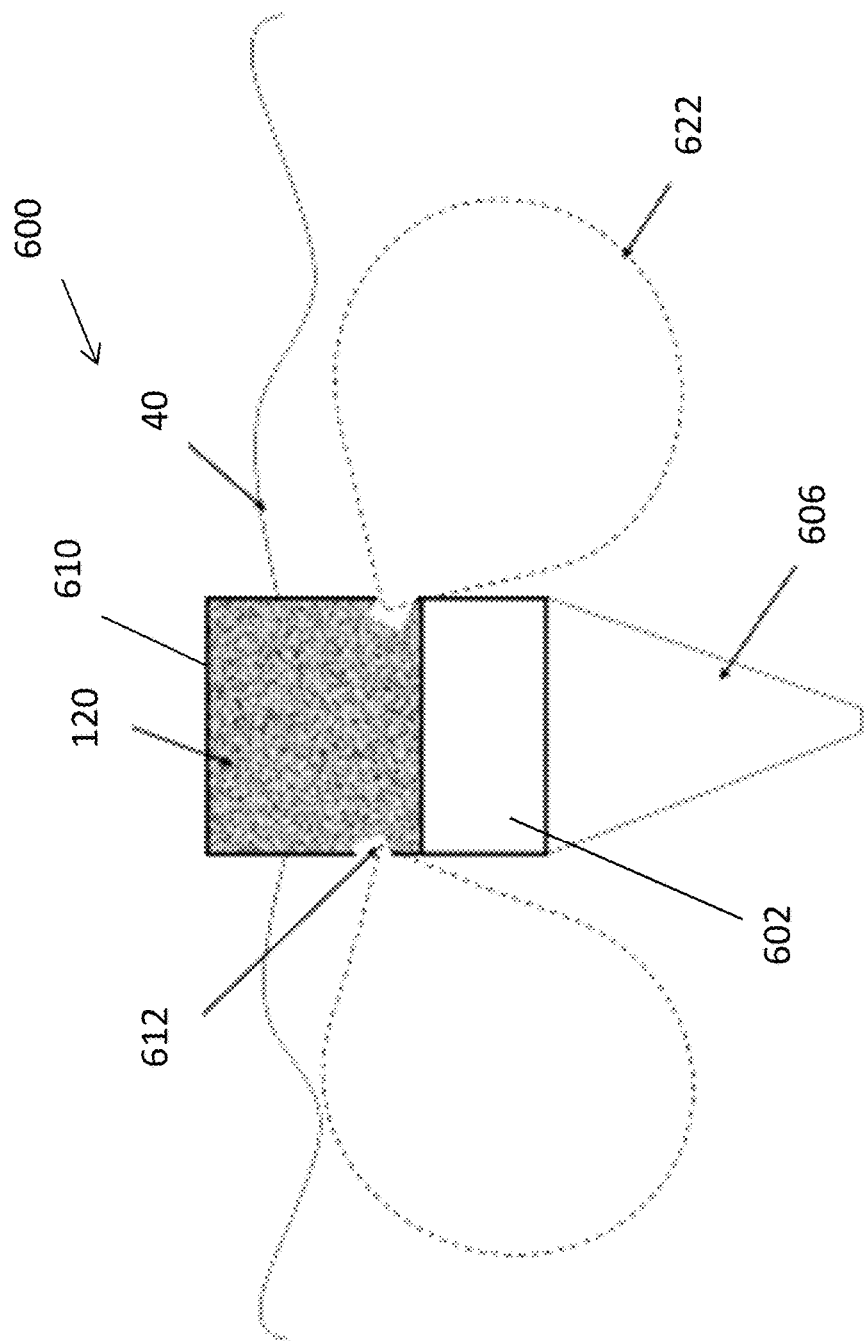

Optionally, altering material 126 is a solvent. A solvent optionally provides for dilution of AI 122 and further optionally for a potential increase in volatilization of the compounded formulation by an azeotropic mixture for which the evaporation temperature of the resultant mixture is lower than that of AI 122 by itself. Optional non limiting examples of an AI 122 combined with an altering material 126 where altering material 126 is a solvent include: metofluthrin and isopropanol, or transfluthrin and an alcohol. Optionally, AI 122 is solid at room temperature due to a relatively high melting point and a solvent provides for an improvement in the volatilization by relying on a phase change from liquid to vapor, instead of solid to vapor. A non-limiting example of an AI 122 that is solid at room temperature is transfluthrin which has a melting point of 32 degrees Celsius. A non-limiting method for integrating such a solid AI 122 into a matrix 124 is described below with reference to FIGS. 4A-4B. In a formulation of an AI 122 of transfluthrin or metofluthrin with a volatile organic solvent, the AI is provided in a range of 20%-95% of the formulation and the solvent in a corresponding range of 80% to 5%.

Optionally, altering material 126 is an encapsulator/emulsion. Combination of AI 122 with an encapsulator results in a particle that degrades over time for long or short-term release of the AI 122 inside depending on the rate of degradation. Additionally or alternatively, an encapsulator is combined with AI 122 to become a porous particle (similar to matrix 124) for containing AI 122 and providing a barrier for rapid evaporation of AI 122 to further regulate the release rate of AI 122. A further advantage of an encapsulator is that the encapsulator AI mixture may be poured into reservoir 110 where it sets, to thereby adapt to the form of reservoir 110 and simplify manufacture of device 100. Non-limiting examples of encapsulators include: nano/microparticle or emulsions of PLGA (Poly Lactic-co-Clycolic Acid), poly (lactid) acid (PLA), chitosan, liposomes, $CaCO_3$ particles, silicon/silica particles, and/or alginate. An example of a combined encapsulator and AI 122 is PLGA and imadacloprid (an insecticide).

Optionally, altering material 126 is an enhancer for combination with AI 122 that makes AI 122 more effective. A non-limiting example of an enhancer is DMSO (dimethylsulfoxide) that provides for improved penetration and uptake of an insecticide combined with DMSO, in target insects.

Optionally, altering material 126 is an exothermic reactant. AI 122 is combined with an exothermic altering material 126 resulting in exothermic reactants increasing the temperature of the active material 120 upon exposure to oxygen, such as when cap 130 is removed. Increased temperature typically increases the evaporation rate. Non-limiting examples of exothermic reactants include powder or rods comprising iron (for exothermic oxidation of the iron when exposed to air), an iron-based compound, vermiculate (hydrated magnesium aluminum silicate), charcoal powder, and sodium chloride.

Optionally, altering material 126 is an oil. Use of an oil typically reduces volatility of the AI. A non-limiting example of such a combination is a pheromone of high volatility and an oleic acid.

FIG. 1D, FIG. 1E and FIG. 1F show exemplary embodiments of a CRD with a diffusion barrier. In some exemplary embodiments, such as shown in FIGS. 1D-1F, device 100 comprises a diffusion barrier 116 that surrounds part or all of active material 120. Diffusion barrier 116 prevents leakage or diffusion of active material 120 such as where reservoir 112 is porous. In some exemplary embodiments, diffusion barrier 116 acts as a secondary release mechanism by absorbing AI 122 and releasing AI 122 at a required release rate. In some exemplary embodiments, more than one diffusion barrier is provided such as illustrated in FIG. 1E with concentric barriers 116A and 116B. When acting as a secondary release mechanism, diffusion barrier 116 optionally includes hydrophobic domains 118 (FIG. 1F), located on the inner walls of barrier 116 to absorb AI 122 from matrix 124, followed by controlled release of AI 122 from barrier 116.

In some exemplary embodiments, active material 120, once inserted inside diffusion barrier 116, becomes suspended and does not make any direct contact with the top or bottom surfaces of reservoir 110, preventing these surfaces from becoming wet from contact with the active material 120. Active material 120 optionally expands and the frictional force between the expanded active material 120 and barrier 116 is such that active material 120 is secured and restrained from moving, even when device 100 is dropped. Moreover, in some exemplary embodiments, diffusion barrier 116 can have one closed end, like a cap. Moreover, some exemplary embodiments of device 100 may include multiple diffusion barriers 116 each holding different active materials 120, allowing multiple formulations of active materials 120 and multiple controlled release profiles.

Device 100 thus provides sustained release of the active ingredient by active or passive mechanisms. A passive controlled release primarily relies on diffusion and natural convection as the main transfer process from reservoir to outside fluid. It should therefore be appreciated that the device 100 provides multiple mechanisms for controlling the passive release of an AI including:

Changing the evaporation rate of the mixture by altering the formulation of active material 120, such as by adding one or more altering materials 126 as described above;

Changing the surface area of the matrix 124 material, such as increasing the surface area to create a greater area for evaporation to thereby increase the release rate;

Changing the permeability of membrane 114, such as choosing a membrane with visible pores 112 for increased release rate or a dense membrane 114 to lower the release rate;

Adding one or more diffusion barriers 116 and varying the thicknesses, absorption rates, diffusion rates, and exposed surface areas of diffusion barriers 116;

Changing the viscosity of the AI 122 and altering material 126 by changing the formulation of active material 120;

Changing the type of matrix 124, such as increasing or decreasing the porosity/permeability of matrix 124. For example, cellulose, which provides a large internal surface area and structural porosity, will cause the formulation to be adsorbed or absorbed and held while limiting the diffusion across the matrix, as well as modulating the overall volatilization.

An active controlled release system can rely on all the characteristics and parameters of the passive system combined other active systems such as:

Changing the temperature of the reservoir 110 and/or reaction between the materials, such as where altering material 126 is an exothermic reactant;

Utilizing active release mechanisms, such as but not limited to a battery and a hot plate (not shown) to increase the temperature of active material 120 to increase volatility of AI 122, or a powered fan (not shown) to provide forced convection to increase mass transfer rates of AI 122.

FIG. 2A and FIG. 2B show sectional illustrations of an exemplary embodiment of a CRD with two chambers. A device 200 provides for controlled release of an AI. Device 200 is functionally similar to device 100 but reservoir 110 comprises two internal chambers 244 and 246 divided by an internal partition 240. A first chamber 244 contains a first material 250 and a second chamber 246 contains a second material 252. Optionally, cap 130 is attached to partition 240 such that removal of cap 130 results in removal or partial removal of partition 240 resulting in the mixture of first material 250 an second material 252. Optionally, cap 130 is not attached to partition 240 to enable separate removal of cap 130 and partition 240. Optionally, mechanisms for partial or full removal of partition 240 are the same as those specified above for cap release mechanism 132. Optionally, either or both of first chamber 244 and second chamber 246 comprise diffusion barriers such as barrier 116 describe above.

In an embodiment, first material 250 comprises matrix 124, and AI 122. Second material 252 comprises altering material 126. Thus when partition 240 is removed, second material 252 is drawn into matrix 124 and reacts with AI 122. As a non-limiting example, first material 250 comprises a sponge 124 containing transfluthrin (AI 122) and second material 252 is a solvent (altering material 126). With removal of partition 240, solvent 126 wicks into sponge 124 to volatize transfluthrin 122 and cause diffusion of the mixture through membrane 114 into the air. Alternatively first material 250 comprises matrix 124, AI 122 and an altering material 126A.

Second material 252 comprises a second altering material 126B. Thus when partition 240 is removed, second material 252 reacts with first material 250. As a non-limiting example, first material 120 comprises a sponge 124 containing transfluthrin (AI 122) and a solvent (altering material 126A) such as isopropanol, while second material 252 comprises an exothermic reactant (altering material 126B). With removal of partition 240, exothermic reactant 126B wicks into sponge 124 to volatize the transfluthrin solvent mixture and cause diffusion of the mixture through membrane 114 into a fluid such as air. In a non-limiting example, where cap 130 is not attached to partition 240, partition 240 is fully or partially removed for activation of an exothermic reaction as exothermic reactant 126B wicks into sponge 124 to first volatize the transfluthrin solvent mixture, followed by removal of cap 130 after a specified time period for diffusion of the mixture through membrane 114 into air.

Thus, in addition to the mechanisms listed above for controlling passive release of an AI, device 200 (and device 300 below) provides further options:

Changing the formulation of the first 250 and second 252 materials (and subsequent materials) to alter the evaporation rate of the AI;

Controlling the permeability of partition 240 and the amount that partition 240 is removed when cap 130 is removed from between internal chambers 244 and 246, such as by changing any of the effective area, thickness, or tortuosity of partition 240.

FIG. 3A and FIG. 3B show sectional illustrations of an exemplary embodiment of a CRD with three chambers. A device 300 provides for controlled release of an AI. Device 300 is functionally similar to devices 100 and 200 but reservoir 110 comprises three internal chambers 344, 346 and 348 divided by internal partitions 340 and 342. A first chamber 344 contains a first material 350, a second chamber 346 contains a second material 352 and a third chamber 348 contains a third material 354. Cap 130 is optionally attached to partitions 340 and 342 such that removal of cap 130 results in removal or partial removal of partitions 340 and 342 resulting in the mixture of first material 350, second material 352, and third material 354. Optionally, cap 130 is not attached to partitions 340 and 342 to enable separate removal of cap 130 and of partitions 340 and 342. Optionally, partitions 340 and 342 are removed simultaneously or sequentially. Optionally, mechanisms for partial or full removal of partitions 340 and 342 are the same as those specified above for cap release mechanism 132. Optionally, any or all of first chamber 344, second chamber 346 or third chamber 348 comprise diffusion barriers such as barrier 116 describe above.

In an embodiment, first material 350 comprises matrix 124, and AI 122. Second material 352 comprises first altering material 126A, and third material 354 comprises second altering material 126B. Thus when partitions 340 and 342 are removed second material 352 and third material 354 are drawn into matrix 124 and react with AI 122.

As a non-limiting example, first material 350 comprises a sponge 124 containing transfluthrin (AI 122), second material 352 is a solvent (altering material 126A) and third material 354 is an exothermic reactant (altering material 126B). With removal of partitions 340 and 342, solvent 126A wicks into sponge 124 to volatize transfluthrin 122, and exothermic reactant 126B wicks into sponge 124 to further volatize the transfluthrin solvent mixture and cause diffusion of the mixture through membrane 114 into the air.

In a non-limiting example, where cap 130 is not attached to partitions 340 and 342, partitions 340 and 342 are fully or partially removed such that solvent 126A wicks into sponge 124 to volatize transfluthrin 122 and exothermic reactant 126B wicks into sponge 124 to first volatize the transfluthrin solvent mixture, followed by removal of cap 130 after a specified time period for diffusion of the mixture through membrane 114 into air. Optionally, the mechanism for removing partitions 340, 342 prevents removal of cap 130 such that a user is forced to first remove the partitions 340, 342 before removal of cap 130.

Reference is now made to FIG. 4A which is a flowchart showing an exemplary process 400 for integrating an AI with a high melting point into a matrix 124. A non-limiting example of an AI that is solid at room temperature is transfluthrin which has a melting point of 32 degrees Celsius. In step 402 the AI is warmed past its melting point to form a liquid form of the AI. In step 404 the matrix is soaked with the liquid form of the AI. Alternatively, the matrix is cooled before exposure to the liquid form of the AI such that the AI solidifies upon contact with the matrix. In step 406 the AI cools and solidifies within and around the matrix to form an active material. Optionally, the cooling is active requiring but not limited to placing the soaked matrix in refrigeration. Alternatively, the cooling is passive where the soaked matrix is left until it cools to room temperature. In step 408 the active material is inserted into the release device such as a reservoir of one of the device embodiments as described herein. As described above with reference to FIGS. 1A-1F, 2A-2B, and 3A-3B, a solvent is used for volatizing the active material and releasing the AI from the matrix.

An alternative method is shown in FIG. 4B which is a flowchart showing an exemplary process 450 for integrating an AI with a high melting point into a matrix 124. In step 452 the AI is combined with a solvent to liquefy the AI. In step 454 the matrix is soaked with the combined solvent/AI. In step 456 the soaked sponge is warmed or placed in an environment such that the solvent evaporates leaving behind the AI that solidifies within and around the matrix to form an active material. In step 458 the active material is inserted into the release device such as a reservoir of one of the exemplary embodiments as described herein. As described above, when the device is activated, a solvent is used for volatizing the active material and releasing the AI from the matrix. In the embodiment of FIG. 4B a lower concentration of AI is impregnated into the matrix than in the embodiment of FIG. 4A.

FIG. 5A, FIG. 5B, FIG. 5C, and FIG. 5D show alternate views and an exploded view of an exemplary embodiment of a CRD. As shown in FIGS. 5A-5D, a CRD 500 comprises a reservoir 510 with multiple chambers 518 each holding an active material 520. Active material 520 is the same as active material 120 and comprises one or more of AI, matrix and altering materials. CRD 500 optionally includes an indicator 508 showing the amount of AI remaining in CRD 500. Indicator 508 is optionally a window on device 500 with a scale and a dye calibrated to have the same or similar volatility as the active material 520 in each chamber to thus show the remaining concentration of the AI in each chamber.

In the illustrations, device 500 is shown as having four chambers 518 but optionally any suitable number of chambers 518 may be provided. Chambers 518 are formed within reservoir 510 by dividers 516. In the embodiment as shown, active materials 520 in each chamber 518 do not come into contact with one another and do not mix. Optionally, dividers 516 can be removed before use to enable mixing of active materials 520 such as in the embodiments of FIGS. 2A-2B and 3A-3B.

Optionally, active materials 520 in each of chambers 518 are of differing formulations. Optionally, each of chambers comprises pores 512 for diffusion of the AI from the corresponding active material 520. Optionally, a grid 514 prevents direct contact of active material 520 with pores 512. A cap 530 seals pores 512 until device 500 is to be used and cap 530 is removed. Optionally, pores 512 of each chamber 518 are covered by separate caps 530. In some embodiments, the number and arrangement of pores 512 are different for each chamber 518 such as shown in FIG. 5D. The illustration of FIG. 5D showing different pore 512 arrangements per chamber 518 should not be considered limiting.

FIG. 5E shows a graph of exemplary dispersion rates for a CRD with multiple chambers. The combination of differing active material 520, chamber 518 size and number/arrangement of pores 512 result in different release characteristics for each chamber 518. Thus, these parameters can be adjusted such that chambers 518 have overlapping release periods such as in the illustrative graph of FIG. 5E showing overlapping release concentrations from two chambers 518 including a large initial release from a first chamber 518 for initial stronger effect of the AI.

In exemplary embodiments where each of chambers 518 contain different formulations of active material combined with an altering material, a formulation of an AI of transfluthrin or metofluthrin mixed with a volatile organic solvent is provided with the AI in a range of 20% to 95% of the formulation, and the solvent in a corresponding range of 80% to 5%. The size and arrangement of pores 512, and the percentage of AI present in a chamber 518 are optionally together designed to provide the required release rates per chamber 518.

FIG. 5F and FIG. 5G show photographs of an exemplary CRD adapted for attachment to clothing. As shown in FIG. 5F, CRD 500 is shaped so as to fit into a standard issued military uniform or vest 20 having a weaving 22. In FIG. 5F, CRD 500A is shown not inserted into weaving 22 in order to clearly show the positioning of pores 512A and 512B. In FIGS. 5F-5G, CRD 500B is shown inserted into weaving 22. As shown, pores 512A and 512B of device 500 are sized and positioned such that pores 512A and 512B are between weaving 22 such that weaving 22 does not block pores 512A and 512B. Holding clip 506 is used for positioning and easy insertion and removal of device 500 into weaves 22. In exemplary embodiments, the spacing between successive weaves 22 is one inch, and weaves have a height of one inch such that the height of pores 512A and 512B is one inch.

FIG. 6 shows an exemplary embodiment of a CRD for releasing an active ingredient such as a larvicide into a fluid environment. Exemplarily, the fluid environment is water 40 or another liquid. In some exemplary embodiments, controlled release larvicides are released from a floating CRD 600 for sustained and prolonged performance such as for up to three months. As with device 100, device 600 comprises active material 120 and variation of release rates of an AI are controlled as for device 100. Optionally, reservoir 610 comprises multiple chambers each with different active materials that combine when the partitions between the chambers are removed such as when device 600 is deployed such as in the embodiments of FIGS. 2A-2B and 3A-3B.

The use of device 600 for controlled release of a larvicide into water requires that device 600 float (have buoyancy) in water 40 and that it not get wet internally, to prevent compromising the device structure. The latter may be achieved for example by adding a super hydro/oleic phobic material layer (such as silica nano-coatings, or fluorinated silanes) on the outside of device 600.

Device 600 comprises an air chamber 602 that allows device 600 to float, a stabilizer 606 that maintains the position of device 600 as it floats, and pores 612 to allow the active ingredient to diffuse into water 40. As shown in FIG. 6, pores 612 release a trail 622 of AI into water 40.

FIG. 7 shows an exemplary embodiment of a CRD for deployment from a flying platform. As shown in FIG. 7, a controlled release system disclosed herein may be dropped from a flying platform such as a drone or a plane. FIG. 7 shows a CRD 700 hanging from a miniature parachute 702. Parachute 702 includes a canopy 704 connected by strings 706 to device 700. Canopy 704 allows device 700 to land softly on land or water. The parachute strings 706 activate device 700 by pulling up a cap 730 covering the pores 712 of device 700. Device 700 comprises an active material 120. Optionally, reservoir 710 comprises multiple chambers each with different active materials that combine when the partitions between the chambers are removed such as when cap 730 is lifted such as in the embodiments of FIGS. 2A-2B and 3A-3B.

Figure 7:
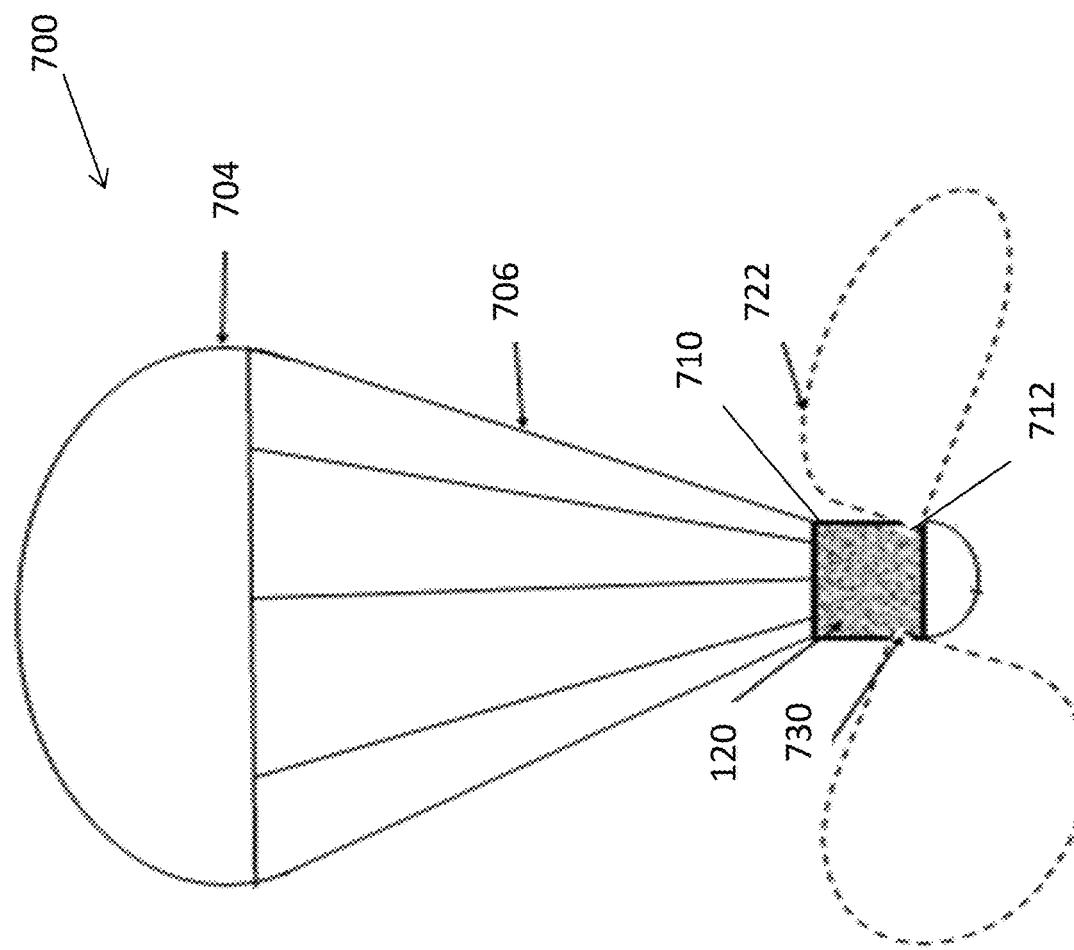

In use, as device 700 is dropped from a flying platform, increased air resistance in canopy 704 increases the pulling force on canopy strings 706, opening device cap 730 and releasing the AI into the surrounding fluid (air or water). Convective forces due to wind during device landing increase mass transfer. By changing parachute landing parameters, a change in force convection can be achieved thus tailoring release rate of the AI. As shown in FIG. 7, pores 712 release a trail 722 of AI into the surrounding fluid.

FIGS. 8A-8D show an exemplary embodiment of a CRD formed from a fold-up reservoir. Exemplarily, CRD 800 is in the shape of a hexagonal cardboard or paper or cellulose-based box described in co-owned U.S. design patent application Ser. No. 29/633,676, titled "Fold-up container/dispenser with a floor and a dispersion platform" and filed Jan. 15, 2018. In an exemplary embodiment, the fold-up container/dispenser is a hexagonal box, shown in FIG. 8A in a closed state and in FIG. 8B in an open state. The box is initially a flat paper or cardboard structure, FIG. 8C, that, upon folding, becomes a 3D structure as in FIGS. 8A-8B.

Figure 8B:
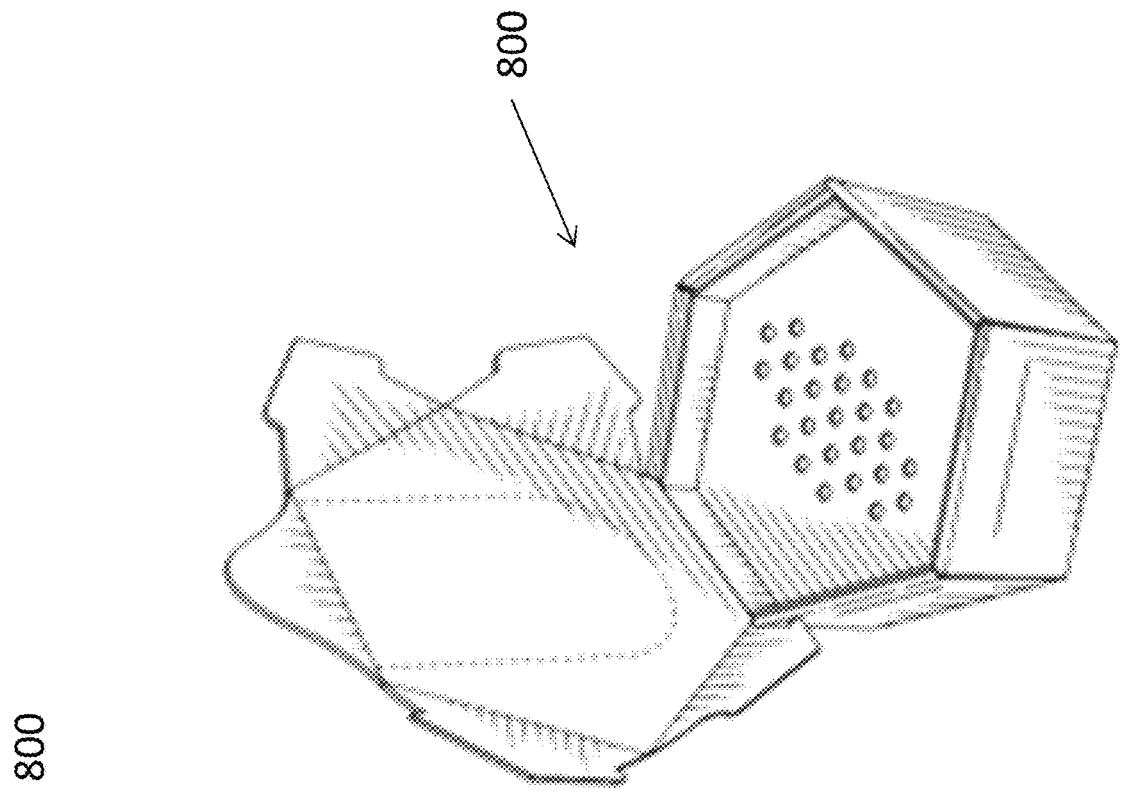
Figure 8A:
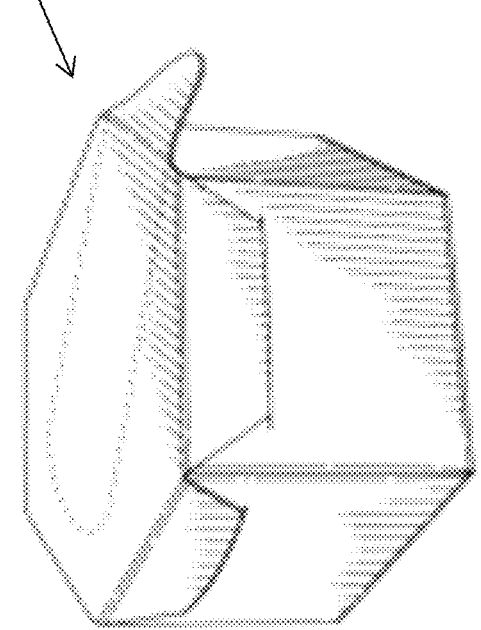
Figure 8D:
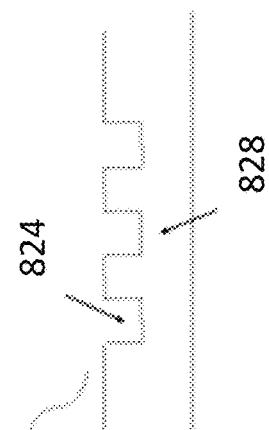
Figure 8C:
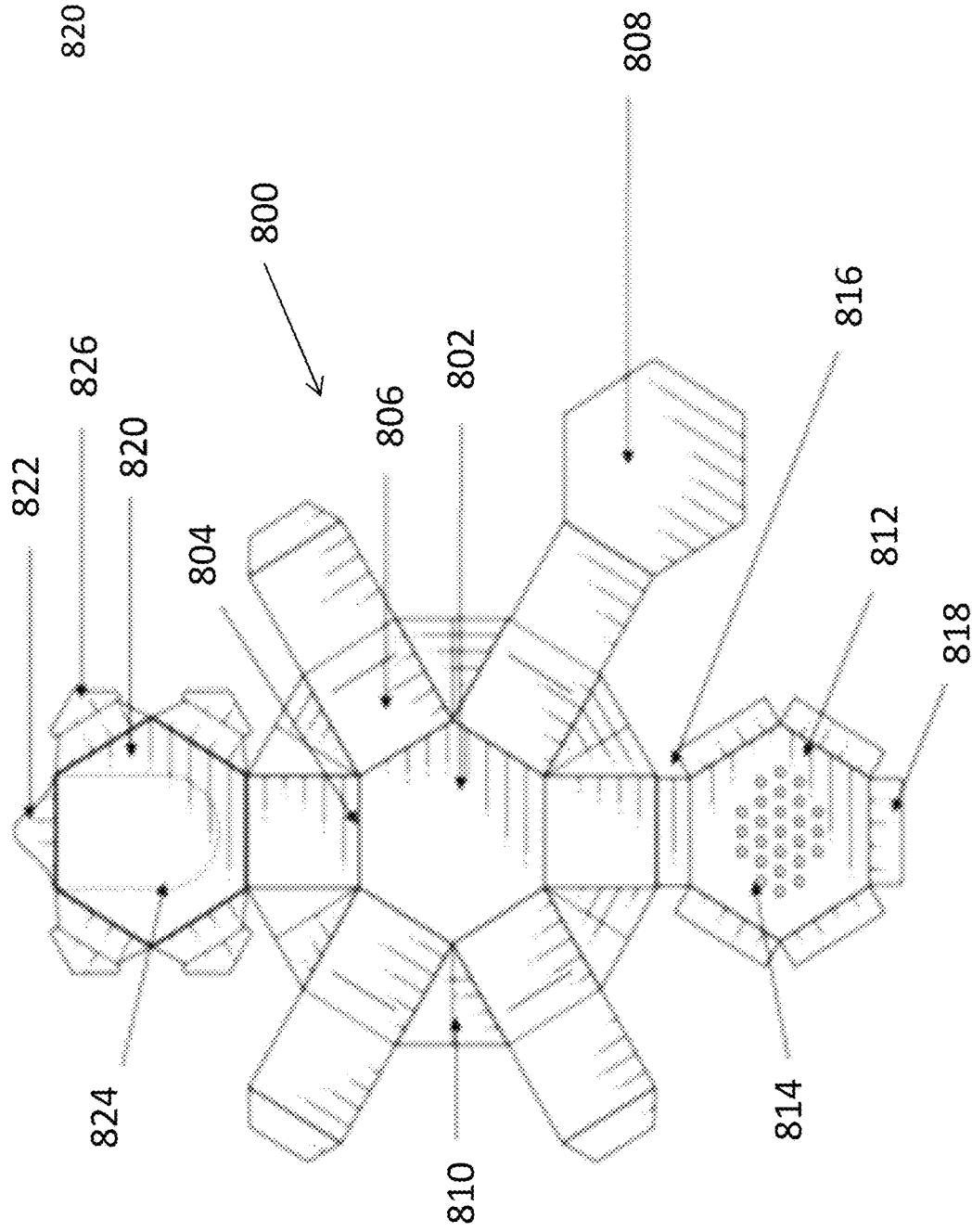

FIG. 8C shows hexagonal box CRD 800 in its 2D shape. Box 800 comprises a box base 802, where a floor 808 of the device will be located upon folding. The base supports the active material 120. Device 800 further comprises hinge regions 804 to allow the parts to fold, box sidewalls 806 to provide lateral confinement to the controlled release system, a box floor 808, where the controlled release device is positioned, a hinge region 810 to allow folding of box floor inwards and a perforated membrane 812 with pores 814 that provide a controlled release mechanism and that can be sized to a desired size to control release kinetics. Device 800 further comprises a hinge region 816 to allow the perforated membrane to fold, a foot pedestal 818 to allow the perforated membrane to anchor on top of the device without displacement, a cap 820 to provide hermeticity to the device and avoid release of active ingredient, a pull tab 822 to allow activation of the device by breaking pre-perforations, pre-perforations 824 on cap 820 to ensure device hermeticity until the device is activated via pull tab, and cap flaps 826 to allow perforated membrane 812 to fit within the hexagonal box. The flaps arrows can be made square or circular to facilitate sealing of device 800. FIG. 8D shows that pre-perforations 824 are not made through the entirety of the cap material (i.e. do not penetrate through cap 820 from one side to the other), leaving a non-perforated section 828 in order to minimize leakage of the AI and vapors while the device is stored.

In the claims or specification of the present application, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended.

It should be understood that where the claims or specification refer to "a" or "an" element, such reference is not to be construed as there being only one of that element.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

While this disclosure describes a limited number of embodiments, it will be appreciated that many variations, modifications and other applications of such embodiments may be made. The disclosure is to be understood as not limited by the specific embodiments described herein, but only by the scope of the appended claims.

What is claimed is:

1. A controlled release device (CRD) comprising:
   a) a reservoir divided into a plurality of chambers by partitions positioned between adjacent chambers, each partition having respective partition planes contacting the adjacent chambers;
   b) a first active material placed in a first chamber of the plurality of chambers and at least one second active material placed in at least one other of the plurality of chambers, wherein the first active material comprises an active ingredient (AI), wherein the at least one second active material comprises one or both of a matrix and an altering material, and wherein the partitions are positioned between adjacent chambers such that full or partial removal of at least one partition results in mixing of the first active material and the at least one second active material to form a mixed active material;
   c) a permeable membrane comprising pores covering the first chamber, wherein the respective partition planes are substantially perpendicular to the permeable membrane; and
   d) a cap positioned over the membrane for sealing the reservoir such that removal of the cap results in controlled release of the AI from the mixed active material through the membrane.

2. The device of claim 1, wherein the AI is one of transfluthrin or metofluthrin and wherein the altering material of the at least one second active material is a volatile organic solvent such that the mixed active material is volatized transfluthrin.

3. The device of claim 1, wherein the AI is one of transfluthrin or metofluthrin and wherein the altering material of a first of at least one second active material is a volatile organic solvent and the altering material of a second of at least one second active material is dimethylsulfoxide (DMSO) such that the mixed active material is volatized transfluthrin or metofluthrin enhanced by DMSO.

4. The device of claim 1, wherein the AI is one of transfluthrin or metofluthrin and the first active material further comprises dimethylsulfoxide (DMSO) for enhancing the transfluthrin wherein the altering material of the at least one second active material is a volatile organic solvent such that the mixed active material is volatized transfluthrin or metofluthrin enhanced by DMSO.

5. The device of any one claim 2, wherein the volatile organic solvent is one of isopropanol, ethanol, methanol, or hexane.

6. The device of any one claim 2, wherein the AI is provided in a concentration of between 20%-95% of the mixed active material.

7. The device of claim 1, wherein the altering material of a first of the at least one second active material is an exothermic reactant such that the mixed active material is the AI at an increased temperature.

8. The device of claim 1, wherein the AI is transfluthrin and wherein the altering material of a first of at least one second active material is a volatile organic solvent and the altering material of a second of at least one second active material is an exothermic reactant such that the mixed active material is volatized transfluthrin that is further volatized by increased temperature caused by the exothermic reactant.

9. The device of claim 7, wherein the exothermic reactant is provided in the form of powder or rods selected from the group consisting of iron, iron-based compounds, vermiculate (hydrated magnesium aluminum silicate), charcoal powder, and sodium chloride.

10. The device of claim 7, wherein the exothermic reactant is an exothermic reactant that is activated when exposed to oxygen such that the exothermic reactant is activated when the cap is removed.

11. The device of claim 1, wherein the AI is one of an insecticide, a spatial repellent, a herbicide or a larvicide.

12. The device of claim 1, wherein the first active material further comprises one or both of a matrix and an altering material.

13. The device of claim 12, wherein the controlled release is determined by a mechanism selected from the group consisting of changing the evaporation rate of the AI, changing the surface area of the matrix, changing the permeability of the membrane, adding one or more diffusion barriers, changing the viscosity of the first active material, changing the type of matrix, changing the temperature of the reservoir, utilizing an active release mechanism, changing the formulation of the first active material, changing the formulation of the at least one second active material, changing the permeability of the plurality of partitions, and a combination thereof.

14. The device of claim 1, wherein the AI is selected from the group consisting of a spatial repellent, an essential oil, a pyrethroid, an insecticide, an organochloride, an organophosphate, a carbamate, a neonicotinoid, a herbicide, an attractant, a larvicide, and a combination thereof.

15. The device of claim 1, wherein the altering material is selected from the group consisting of a solvent, an encapsulator, an enhancer, an exothermic reactant, an oil and a combination thereof.

16. The device of claim 12, wherein the matrix is selected from the group consisting of a porous material, a synthetic material, a material reactive to the altering material, and a combination thereof.

17. The device of claim 1, further comprising at least one diffusion barrier.

18. The device of claim 17, wherein the diffusion barrier comprises at least one hydrophobic domain.

19. The device of claim 1, further comprising a cap release mechanism selected from the group consisting of a mechanical cap release mechanism, a breakable cap release mechanism, an electrothermal rupture release mechanism, an electro-thermal-stress rupture release mechanism, an ultrasound cap release mechanism, a pH-based cap release mechanism, an optical-based release mechanism, and a combination thereof.

20. The device of claim 1, wherein the device is adapted to be wearable.

21. The device of claim 1, further comprising an indicator for showing the amount of AI remaining in the device wherein the indicator comprises a scale and a dye calibrated to have the same volatility as the mixed active material to thus show the remaining concentration of AI in the device.

22. The device of claim 20, wherein the pores are positioned so as to be exposed when the device is inserted into periodically spaced weavings of a vest.

* * * * *